(12) United States Patent
Okatake et al.

(10) Patent No.: US 12,082,915 B2
(45) Date of Patent: Sep. 10, 2024

(54) MAGNETIC FIELD MEASUREMENT DEVICE, MAGNETIC FIELD MEASUREMENT METHOD, AND RECORDING MEDIUM HAVING MAGNETIC FIELD MEASUREMENT PROGRAM RECORDED THEREON

(71) Applicant: Asahi Kasei Microdevices Corporation, Tokyo (JP)

(72) Inventors: Shigeki Okatake, Tokyo (JP); Makoto Kataoka, Tokyo (JP); Takenobu Nakamura, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 663 days.

(21) Appl. No.: 17/241,106

(22) Filed: Apr. 27, 2021

(65) Prior Publication Data
US 2021/0345898 A1 Nov. 11, 2021

(30) Foreign Application Priority Data
May 8, 2020 (JP) .................................. 2020-082873

(51) Int. Cl.
*G01R 5/02* (2006.01)
*A61B 5/024* (2006.01)
(Continued)

(52) U.S. Cl.
CPC ...... *A61B 5/02405* (2013.01); *G01R 33/0011* (2013.01); *G01R 33/0094* (2013.01); *G01R 33/02* (2013.01)

(58) Field of Classification Search
CPC .......... A61B 5/02405; A61B 2562/046; A61B 5/243; A61B 5/743; G01R 33/0011;
(Continued)

(56) References Cited

U.S. PATENT DOCUMENTS 11,454,679 B2   9/2022  Okatake
2003/0097056 A1  5/2003  Suzuki
(Continued)

FOREIGN PATENT DOCUMENTS

JP   H06154185 A   6/1994
JP   H06245916 A   9/1994
(Continued)

OTHER PUBLICATIONS

Kei On et al., "Integral Value of JT Interval in Magnetocardiography is Sensitive to Coronary Stenosis and Improves Soon After Coronary Revascularization",Magnetocardiography and Coronary Disease, Circulation Journal vol. 71, Oct. 2007,pp. 1586-1592.
(Continued)

*Primary Examiner* — Alvaro E Fortich

(57) ABSTRACT

Provided is a magnetic field measurement device which includes a magnetic sensor array that is composed of a plurality of magnetic sensor cells, each of which has a magnetic sensor and an output unit for outputting an output signal, arranged at lattice points between two curved surfaces, each of which is bent in one direction, so as to be three-dimensionally arranged, and is capable of detecting an input magnetic field in three-axial directions, a measurement data acquisition unit configured to acquire measurement data measured by the magnetic sensor array, and a magnetic field reconstruction unit configured to reconstruct a magnetic field of a component orthogonal to a virtual sensor array plane with respect to one or more positions on the virtual sensor array plane, which is a plane specified in a three-dimensional space, using the measurement data.

20 Claims, 16 Drawing Sheets

(51) Int. Cl.
*G01R 33/00* (2006.01)
*G01R 33/02* (2006.01)

(58) Field of Classification Search
CPC ............... G01R 33/0094; G01R 33/02; G01R 33/0017; G01R 33/0206; G01R 33/0041; G01R 33/091
See application file for complete search history.

(56) References Cited

U.S. PATENT DOCUMENTS

| | | |
|---|---|---|
| 2006/0031038 A1 | 2/2006 | Simola |
| 2008/0294386 A1 | 11/2008 | Taulu |
| 2012/0219195 A1 | 8/2012 | Wu |
| 2013/0214774 A1 | 8/2013 | Cesaretti |
| 2013/0317337 A1 | 11/2013 | Wu |
| 2013/0324832 A1 | 12/2013 | Wu |
| 2015/0128431 A1 | 5/2015 | Kuo |
| 2016/0299593 A1* | 10/2016 | Christiansson ....... G06F 3/0416 |
| 2017/0248665 A1 | 8/2017 | Ludwig |
| 2017/0299662 A1* | 10/2017 | Nagasaka ............... A61B 5/243 |
| 2017/0350947 A1* | 12/2017 | Lacouture .......... G01R 33/0005 |
| 2018/0110436 A1* | 4/2018 | Marcus ................ A61B 5/6823 |
| 2018/0340987 A1 | 11/2018 | Latham |
| 2019/0133478 A1 | 5/2019 | Varcoe |
| 2019/0328263 A1* | 10/2019 | Marcus .................. A61B 5/361 |
| 2021/0161420 A1 | 6/2021 | Nakamura |
| 2021/0345898 A1 | 11/2021 | Okatake |

FOREIGN PATENT DOCUMENTS

| | | |
|---|---|---|
| JP | H09164123 A | 6/1997 |
| JP | H114816 A | 1/1999 |
| JP | H11276451 A | 10/1999 |
| JP | 2001087237 A | 4/2001 |
| JP | 2001104268 A | 4/2001 |
| JP | 2002177233 A | 6/2002 |
| JP | 2003334174 A | 11/2003 |
| JP | 2007125236 A | 5/2007 |
| JP | 2012152514 A | 8/2012 |
| JP | 2016178994 A | 10/2016 |
| JP | 2021016630 A | 2/2021 |

OTHER PUBLICATIONS

F Chella et al., "Calibration of a multichannel MEG system based on the Signal Space Separation method" Physics in Medicine and Biology. 57 (2012) 4855-4870.

Samu Taulu et al., "Presentation of electromagnetic multichannel data: The signal space separation method", J Appl Phys 97, 124905, pp. 1-10, (2005).

Samu Taulu et al., "Applications of the Signal Space Separation Method", IEEE Transactions On Signal Processing, vol. 53, No. 9, Sep. 2005, pp. 3359-3372.

* cited by examiner

MAGNETIC FIELD MEASUREMENT DEVICE, MAGNETIC FIELD MEASUREMENT METHOD, AND RECORDING MEDIUM HAVING MAGNETIC FIELD MEASUREMENT PROGRAM RECORDED THEREON

The contents of the following Japanese patent application are incorporated herein by reference:
NO. 2020-082873 filed in JP on May 8, 2020

BACKGROUND

1. Technical Field

The present invention relates to a magnetic field measurement device, a magnetic field measurement method, and a recording medium having a magnetic field measurement program recorded thereon.

2. Related Art

Patent Document 1 describes "a plurality of current arrow maps, which are vectors of the current flowing in a cardiac magnetic field, are generated from a cardiac magnetic field signal measured by a magnetocardiographic measurement device".

PRIOR ART DOCUMENT

Patent Document

Patent Document 1: Japanese Patent Application Publication No. 2016-178994

SUMMARY

In a first aspect of the invention, a magnetic field measurement device is provided. The magnetic field measurement device may include a magnetic sensor array which is composed of a plurality of magnetic sensor cells, each of which includes a magnetic sensor and an output unit for outputting an output signal, arranged at lattice points between two curved surfaces, each of which is bent in one direction, so as to be three-dimensionally arranged, and are capable of detecting an input magnetic field in three-axial directions. The magnetic field measurement device may include a measurement data acquisition unit configured to acquire measurement data measured by the magnetic sensor array. The magnetic field measurement device may include a magnetic field reconstruction unit configured to reconstruct the magnetic field of the component orthogonal to the virtual sensor array plane with respect to one or more positions on the virtual sensor array plane, which is the plane specified in the three-dimensional space, using the measurement data.

Each of the plurality of magnetic sensor cells may further include a magnetic field generation unit that generates a feedback magnetic field to reduce an input magnetic field detected by the magnetic sensor at a magnitude according to the output signal. The output unit may output the output signal according to a feedback current that flows for the magnetic field generation unit to generate the feedback magnetic field.

Each of the magnetic sensors may include a magnetoresistive element and two magnetic flux concentrators arranged at both ends of the magnetoresistive element. The magnetoresistive element may be arranged at a position sandwiched by the two magnetic flux concentrators.

The magnetic field generation unit may include a feedback coil that is wrapped along an axial direction of a magnetic field to be detected by the magnetic sensor so as to surround the magnetoresistive element and the two magnetic flux concentrators.

The magnetic field reconstruction unit may reconstruct a magnetic field of a component orthogonal to the virtual sensor array plane with respect to a plurality of positions on the virtual sensor array plane. The magnetic field measurement device may further include a current map generation unit that uses a magnetic field reconstructed with respect to a plurality of positions on the virtual sensor array plane to generate a current map in which a state of an active current due to an electrical activity of an object to be measured is projected onto the virtual sensor array plane.

The current map generation unit may generate a current arrow map showing current vectors at the plurality of positions based on a difference between the magnetic field reconstructed with respect to each of the plurality of positions on the virtual sensor array plane and the magnetic field reconstructed with respect to the adjacent positions.

The magnetic field measurement device may further include a signal space separation unit that performs signal separation on the spatial distribution of the input magnetic field indicated by the measurement data based on a basis vector calculated from the orthonormal function and the position and magnetic sensitivity of each magnetic sensor of the magnetic sensor array.

The magnetic field reconstruction unit may reconstruct the magnetic field of the measurement target magnetic field component, from which the disturbance magnetic field component is separated, with respect to one or more positions on the virtual sensor array plane based on the result obtained by the signal separation.

A cardiac magnetic field which is the magnetic field generated by the electrical activity of the heart may be a measurement target, and the virtual sensor array plane may be specified directly above (front surface) the chest of the object to be measured.

In a second aspect of the invention, a magnetic field measurement method is provided. The magnetic field measurement method may include acquiring measurement data measured by a magnetic sensor array which is composed of a plurality of magnetic sensor cells, each of which includes the magnetic sensor and an output unit for outputting an output signal, arranged at lattice points between two curved surfaces, each of which is bent in one direction, so as to be three-dimensionally arranged, and is capable of detecting an input magnetic field in three-axial directions. The magnetic field measurement method may include reconstructing the magnetic field of the component orthogonal to the virtual sensor array plane with respect to one or more positions on the virtual sensor array plane, which is the plane specified in the three-dimensional space, using the measurement data.

In a third aspect of the invention, a recording medium having a magnetic field measurement program recorded thereon is provided. The magnetic field measurement program may executed by a computer. The magnetic field measurement program may cause the computer to function as a measurement data acquisition unit which acquires measurement data measured by a magnetic sensor array which includes a plurality of magnetic sensor cells, each of which includes the magnetic sensor and an output unit for outputting an output signal, arranged at lattice points between two curved surfaces, each of which is bent in one direction, so as to be three-dimensionally arranged, and is capable of detecting an input magnetic field in three-axial directions. The magnetic field measurement program may cause the computer to function as a magnetic field reconstruction unit which reconstructs the magnetic field of the component orthogonal to the virtual sensor array plane with respect to one or more positions on the virtual sensor array plane, which is the plane specified in the three-dimensional space, using the measurement data.

The summary clause does not necessarily describe all necessary features of the embodiments of the present invention. The present invention may also be a sub-combination of the features described above.

DESCRIPTION OF EXEMPLARY EMBODIMENTS

Hereinafter, the invention will be described through embodiments, but the following embodiments do not limit the invention according to the claims. In addition, not all of the combinations of features described in the embodiments are essential to the solving means of the invention.

Figure 1:
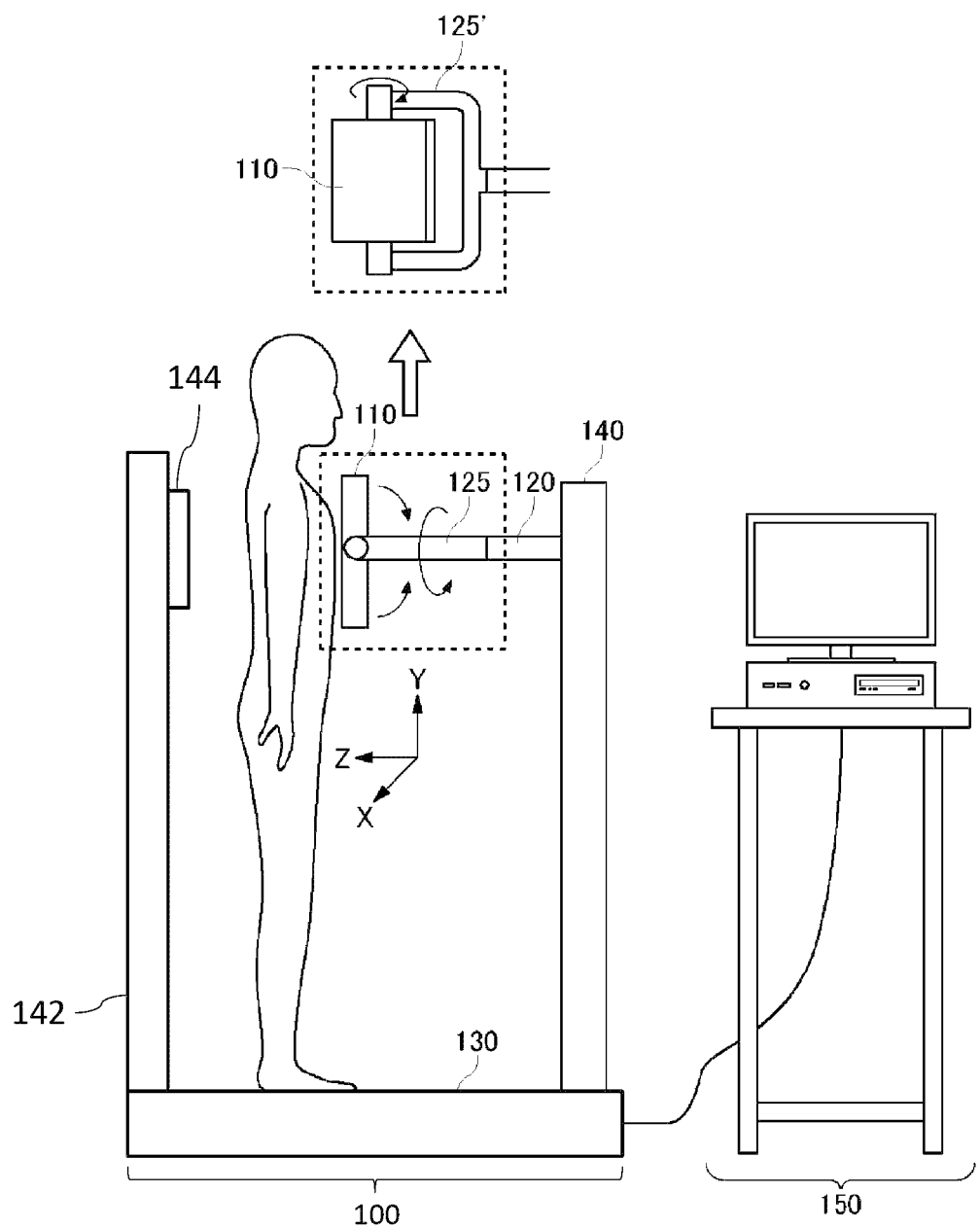
FIG. 1 illustrates the configuration of a magnetic field measurement device 10 according to this embodiment.

FIG. 1 illustrates the configuration a magnetic field measurement device 10 according to this embodiment. The magnetic field measurement device 10 measures a magnetic field by a three-dimensional magnetic sensor array which is capable of detecting an input magnetic field in three-axial directions. Then, the magnetic field measurement device 10 according to this embodiment reconstructs the magnetic field on a virtual sensor array plane using measurement data which is measured by the magnetic sensor array. In this embodiment, a case where the magnetic field measurement device 10 is a magnetocardiographic measurement device for measuring a cardiac magnetic field that is a magnetic field generated by electrical activities of human heart will be described as an example. However, the invention is not limited to this. The magnetic field measurement device 10 may be used for measuring cardiac magnetic fields of living bodies other than humans, or may be used for measuring biological magnetic fields other than the cardiac magnetic field such as a brain magnetic field. In addition, the magnetic field measurement device 10 may be used for magnetic flaw inspection to detect the surface of a steel material or a welding portion and surface scratches or the like.

The magnetic field measurement device 10 includes a main body 100 and an information processing unit 150. The main body 100 is a component for sensing the cardiac magnetic field of a subject, and includes a magnetic sensor unit 110, a head 120, a drive unit 125, a base portion 130, a pole portion 140, a support portion 142, and a calibration magnetic field generation unit 144.

The magnetic sensor unit 110 is arranged at a position toward the heart in the subject's chest at the time of measuring the cardiac magnetic field, and senses the cardiac magnetic field of the subject. The head 120 supports the magnetic sensor unit 110, and makes the magnetic sensor unit 110 face the subject when measuring the cardiac magnetic field. In addition, the head 120 may be stretchable in the Z axis direction, and stretches when performing calibration so as to make the magnetic sensor unit 110 face the calibration magnetic field generation unit 144. The drive unit 125 is provided between the magnetic sensor unit 110 and the head 120, and changes the direction of the magnetic sensor unit 110 with respect to the head 120 when performing calibration. The drive unit 125 according to this embodiment includes a first actuator capable of rotating the magnetic sensor unit 110 by 360 degrees about the Z axis in the drawing and a second actuator for rotating the magnetic sensor unit 110 about the axis (in the state in the drawing, X axis) perpendicular to the Z axis, and changes the azimuth angle and the zenith angle of the magnetic sensor unit 110 using these actuators. As illustrated as the drive unit 125 in the drawing, the drive unit 125 has a Y shape when viewed from the Y axis direction in the drawing. The second actuator can rotate the magnetic sensor unit 110 by 360 degrees about the X axis center in the drawing.

The base portion 130 is a base for supporting other members and, in this embodiment, is a stand where the subject rides at the time of measuring the cardiac magnetic field. The pole portion 140 supports the head 120 to the height of the subject's chest. The pole portion 140 may be stretchable in the vertical direction to adjust the height of the magnetic sensor unit 110 to the height of the subject's chest.

The support portion 142 supports the calibration magnetic field generation unit 144 to be at the same height as the magnetic sensor unit 110 at the time of calibration. Note that in the above description, a case where the head 120 is stretched to make the magnetic sensor unit 110 face the calibration magnetic field generation unit 144 when performing calibration has been described as an example. However, the invention is not limited to this. The support portion 142 may be moved in the Z axis direction such that the calibration magnetic field generation unit 144 may become movable between a calibration position for facing the magnetic sensor unit 110 and a retracting position for retreating from the calibration position.

The calibration magnetic field generation unit 144 generates a calibration magnetic field at the time of calibration. Such a calibration magnetic field may be an AC magnetic field. As an example, the calibration magnetic field may be a sinusoidal wave of frequency f0, or may be the sum of sinusoidal waves of a plurality of frequencies (for example, frequency f0, frequency f1 (>frequency f0), frequency f2 (>frequency f1), etc.). The cardiac magnetic field, which is one magnetic field to be measured by the magnetic field measurement device 10, has no DC components. Accordingly, since the magnetic field measurement device 10 only performs the calibration of the magnetic sensor using the calibration magnetic field which is an AC magnetic field, there is no need to execute the calibration of the magnetic sensor for the DC offset of the magnetic sensor and the offset drift of a significantly low frequency (for example, 0.1 Hz or less).

Here, in general, the higher the frequency, the smaller the environmental magnetic field. For example, the environmental magnetic field is in the order of tens of pT in a band higher than 50 Hz, which is the same level as the peak of the cardiac magnetic field which is one of the magnetic fields to be measured by the magnetic field measurement device 10 according to this embodiment. Therefore, the calibration magnetic field generation unit 144 may generate an AC magnetic field at a frequency (frequency f0>50 Hz) higher than 50 Hz as the calibration magnetic field. That is, the signal frequency of the cardiac magnetic field is mostly lower than 20 Hz. Thus, the frequency of the AC magnetic field as the calibration magnetic field may be higher than the frequency band of the magnetic field to be measured.

In addition, generally, 50 Hz and 60 Hz are used as a frequency of commercial power sources, for example. Therefore, there is a power source noise at the multipliers of the frequency of these commercial power sources. Therefore, the calibration magnetic field generation unit 144 may use a frequency which is higher than the frequency of the magnetic field to be measured as the frequency of an AC magnetic field, and avoids the multipliers of the frequency of the commercial power sources. As an example, the calibration magnetic field generation unit 144 may use a frequency higher than 50 Hz, which avoids the integer multipliers of 50 Hz and/or 60 Hz. Thereby, since the environmental magnetic field can be suppressed to the order of tens of pT, the calibration magnetic field generation unit 144 is sufficient to only generate the calibration magnetic field which is weak enough to ignore the environmental noise, for example, about tens of nT. That is, with the use of such a frequency as the frequency of an AC magnetic field, the magnetic field measurement device 10 has no need to generate a strong magnetic field as the calibration magnetic field.

The calibration magnetic field generation unit 144 may have a plurality of calibration coils, each of which generates the calibration magnetic field. Then, the calibration magnetic field generation unit 144 may receive a clock signal for calibration described later, and add the clock signal to each of the plurality of calibration coils so as to generate an AC magnetic field according to the frequency of the clock signal from each of the plurality of calibration coils. For example, the calibration magnetic field generation unit 144 may respectively include at least three or more calibration coils which generate the calibration magnetic field in the different axial directions. Then, these different axial directions may be the axial directions orthogonal to each other. As an example, the calibration magnetic field generation unit 144 may include a plurality of three-axial calibration coils which generate the calibration magnetic field in three-axial directions (for example, the X axis direction, the Y axis direction, and the Z axis direction) orthogonal to each other. Thereby, the magnetic field measurement device 10 calibrates the magnetic sensor using the plurality of calibration magnetic fields obtained, each generating a primary independent three-axial magnetic field from a different position, so that the accuracy of calibration can be improved.

In addition, when performing calibration using such an AC magnetic field, the generation of eddy currents needs to be suppressed. Therefore, the housing of the calibration coil which generates the calibration magnetic field may be formed by a resin material or the like having low electrical conductivity.

The information processing unit 150 is a component for outputting by processing data measured by the main body 100, and displaying and/or printing the data or the like. The information processing unit 150 may be a computer such as a PC (personal computer), a tablet computer, a smart phone, a workstation, a server computer, or a general purpose computer, or may be a computer system having a plurality of computers connected thereto. Instead, the information processing unit 150 may be a dedicated computer which is designed for information processing of the magnetic field measurement, or may be a dedicated hardware realized by a dedicated circuit.

Figure 2:
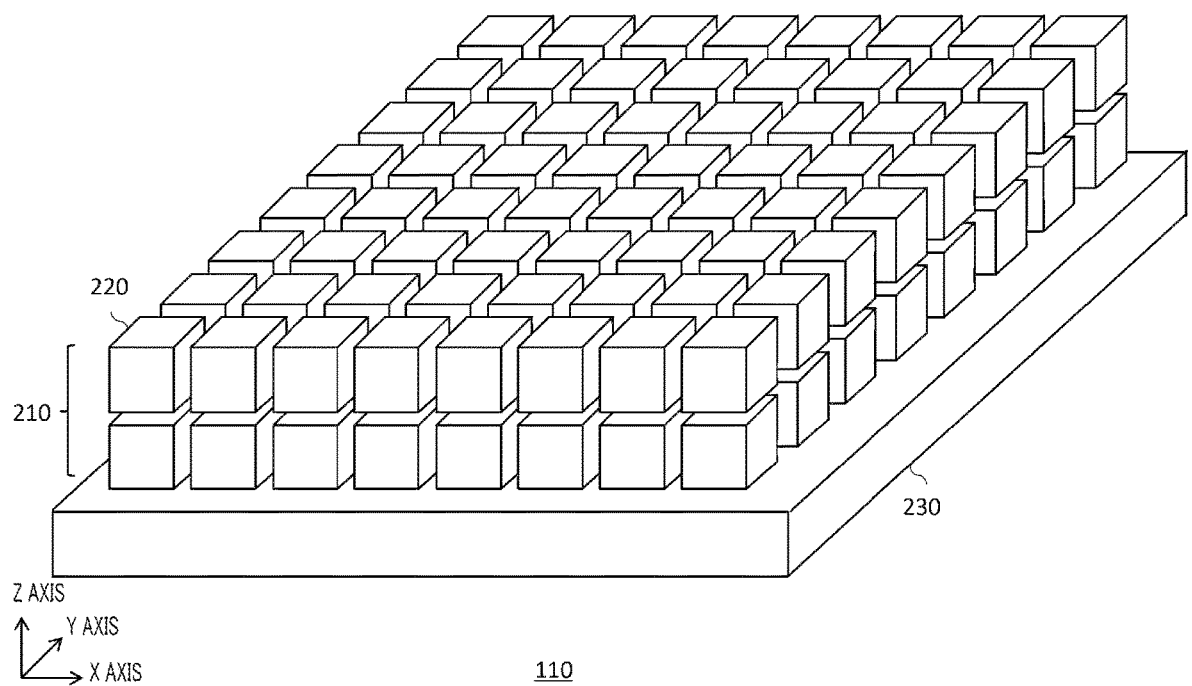
FIG. 2 illustrates the configuration of a magnetic sensor unit 110 according to this embodiment.

FIG. 2 illustrates the configuration of the magnetic sensor unit 110 according to this embodiment. The magnetic sensor unit 110 includes a magnetic sensor array 210 and a sensor data collection unit 230. The magnetic sensor array 210 includes a plurality of magnetic sensor cells 220, and can detect an input magnetic field in three-axial directions. This drawing illustrates a case where the plurality of magnetic sensor cells 220 (for example, total 128 magnetic sensor cells 220: 8 in the X direction, 8 in the Y direction, and 2 in the Z direction) are arranged in the magnetic sensor array 210 in each of the X direction, the Y direction, and the Z direction.

The sensor data collection unit 230 is electrically connected to the plurality of magnetic sensor cells 220 included in the magnetic sensor array 210 (not illustrated), and collects sensor data (output signals) from the plurality of magnetic sensor cells 220 to supply the data to the information processing unit 150.

Figure 3:
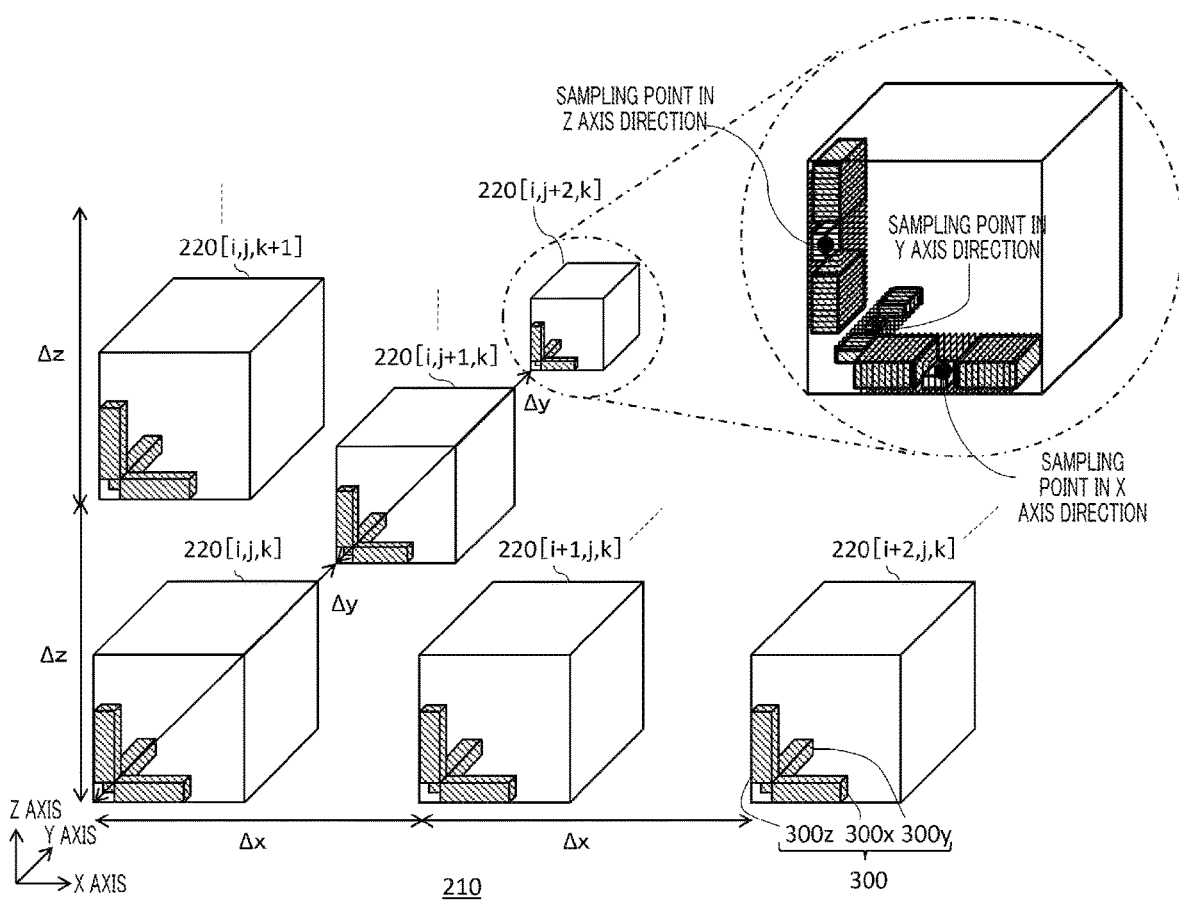
FIG. 3 illustrates the configuration of a magnetic sensor cell 220 in a magnetic sensor array 210 according to this embodiment.

FIG. 3 illustrates the configuration of the magnetic sensor cell 220 in the magnetic sensor array 210 according to this embodiment. Each of the plurality of magnetic sensor cells 220 includes at least one sensor unit 300 which includes the magnetoresistive element. This drawing illustrates a case where each of the plurality of magnetic sensor cells 220 includes three sensor units 300$x$ to 300$z$ (collectively referred to as "sensor unit 300"), and can detect the input magnetic field in three-axial directions as an example. However, none of the plurality of magnetic sensor cells 220 is limited to include three sensor units 300$x$ to 300$z$, but the input magnetic field in the three-axial directions may be detected by at least a part of the magnetic sensor array 210.

At this time, as described later, in a case where each spherical harmonic function is spatially sampled by the magnetic sensor array 210, it is necessary to detect dependency on the spatial frequency related to angular momentum in the magnetic field. Therefore, the arrangement position of each sensor unit 300 in the magnetic sensor array 210 may be arranged at least as unbiasedly as possible in the direction at the azimuth angle and the direction at the zenith angle. For the same reason, the sensor unit may be arranged at least as unbiasedly as possible in the direction at the azimuth angle and the direction of the zenith angle even in the magneto-sensitive axis of each sensor in the magnetic sensor array 210. The sensor unit 300x is arranged along the X axis direction, and can detect the magnetic field in the X axis direction. In addition, the sensor unit 300y is arranged along the Y axis direction, and can detect the magnetic field in the Y axis direction. In addition, the sensor unit 300z is arranged along the Z axis direction, and can detect the magnetic field in the Z axis direction. As illustrated by an enlarged view indicated with a dashed line in this drawing, each sensor unit 300 in this embodiment respectively has magnetic flux concentrators arranged at both ends of the magnetoresistive element. Therefore, each sensor unit 300 can clarify a sampling point in the space in each axial direction by sampling a spatial distribution of the magnetic field using the magnetoresistive element arranged at a narrow position sandwiched by the magnetic flux concentrators. The details of the configuration of each sensor unit 300 is described later.

The plurality of magnetic sensor cells 220 are arranged at equal intervals of $\Delta x$ along the X axis direction, $\Delta y$ along the Y axis direction, and $\Delta z$ along the Z axis direction. The position of each magnetic sensor cell 220 in the magnetic sensor array 210 is represented by a set [i, j, k] of position i in the X direction, position j in the Y direction, and position k in the Z direction. Here, i is an integer satisfying $1 \leq i \leq Nx$ (Nx represents the number of magnetic sensor cells 220 arranged in the X direction), j is an integer satisfying $1 \leq j \leq Ny$ (Ny represents the number of magnetic sensor cells 220 arranged in the Y direction), and k is an integer satisfying $1 \leq k \leq Nz$ (Nz represents the number of magnetic sensor cells 220 arranged in the Z direction). Note that in the above description, a case where the plurality of magnetic sensor cells 220 are arranged at equal intervals along each axial direction has been described as an example. However, the invention is not limited to this. The plurality of magnetic sensor cells 220 may be respectively arranged at different intervals, for example, in at least any one axial direction of the X axis direction, the Y axis direction, and the Z axis direction.

In this drawing, the three-axial directions of the magnetic field detected by the sensor units 300x, 300y, and 300z are the same directions as the three-dimensional directions in which the magnetic sensor cells 220 are arranged. Thereby, it becomes easy to grasp each component of the distribution of the measurement magnetic field. However, the three-axial directions of the magnetic field to be detected and the three-dimensional directions where the magnetic sensor cells 220 are arranged may be different. For example, as the three-axial directions of the magnetic field to be detected, the r axis, the θ axis, and the pp axis of the polar coordinate system may be used instead of the X axis, the Y axis, and the Z axis. In addition, as the three-dimensional directions for arranging the magnetic sensor cells 220, the r axis, the θ axis, and the φ axis of the polar coordinate system may be used instead of the X axis, the Y axis, and the Z axis. In a case where the three-axial directions of the magnetic field to be detected are different from the three-dimensional directions for arranging the magnetic sensor cells 220, the design freedom of the magnetic sensor array 210 can be increased without being constrained by the arrangement of the sensor units 300 in the magnetic sensor cell 220, and the arrangement direction of the magnetic sensor cells 220. In this case, the magnetic sensor cell 220 can be configured small. Thus, it is possible to miniaturize the magnetic sensor array 210 having such a plurality of magnetic sensor cells 220.

Figure 4:
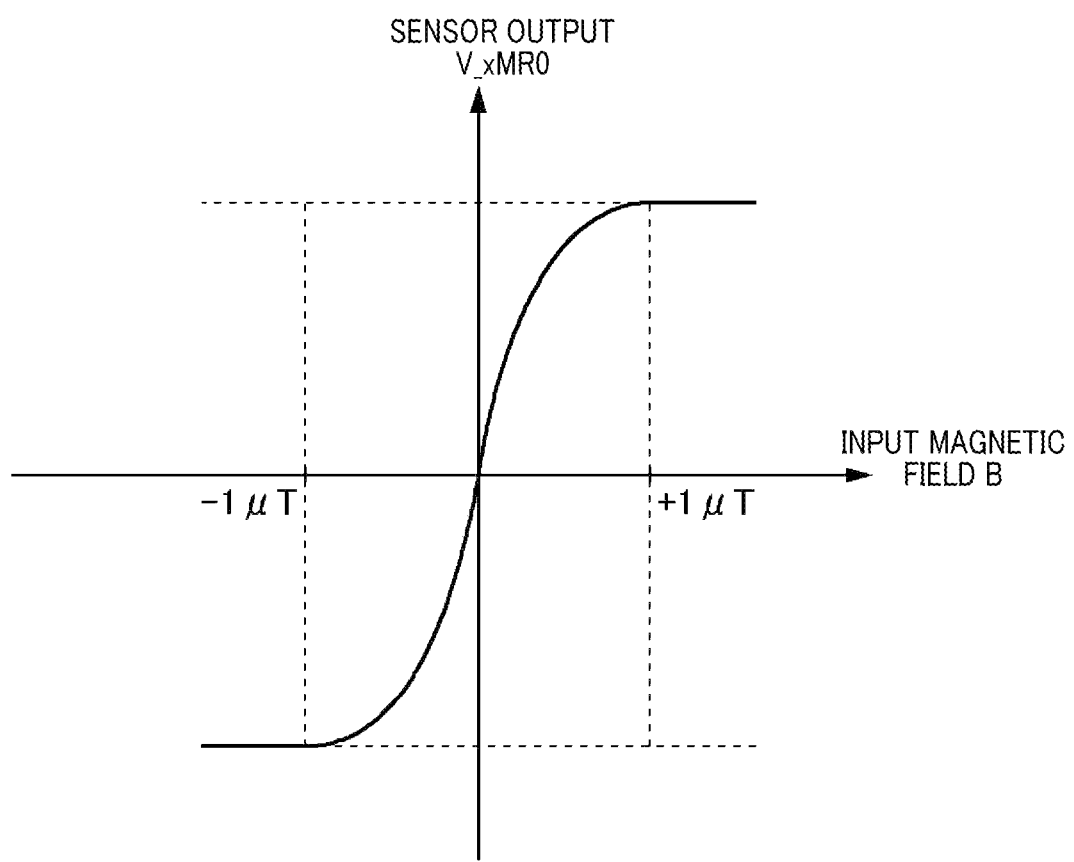
FIG. 4 illustrates an example of the input/output characteristics of a magnetic sensor having a magnetoresistive element according to this embodiment.

FIG. 4 illustrates an example of the input/output characteristics of the magnetic sensor which includes the magnetoresistive element according to this embodiment. In this drawing, the horizontal axis represents the magnitude B of the input magnetic field which is input to the magnetic sensor, and the vertical axis represents the magnitude V_xMR0 of the output signal of the magnetic sensor. The magnetic sensor includes, for example, such as a giant magneto-resistance (GMR) element or a tunnel magneto-resistance (TMR) element, and detects the magnitude of the magnetic field in a predetermined one axial direction.

Such a magnetic sensor has a high magnetic sensitivity which is a slope of the output signal V_xMR0 with respect to the input magnetic field B, and can detect a minute magnetic field having a magnitude of about 10 pT. On the other hand, the output signal V_xMR0 of the magnetic sensor is saturated, for example, at about an absolute value of 1 pT of the input magnetic field B, a good linearity range of the input/output characteristics is narrow. Therefore, if such a magnetic sensor is added with a closed loop which generates a feedback magnetic field, the linearity of the magnetic sensor can be improved. Next, such a magnetic sensor is described.

Figure 5:
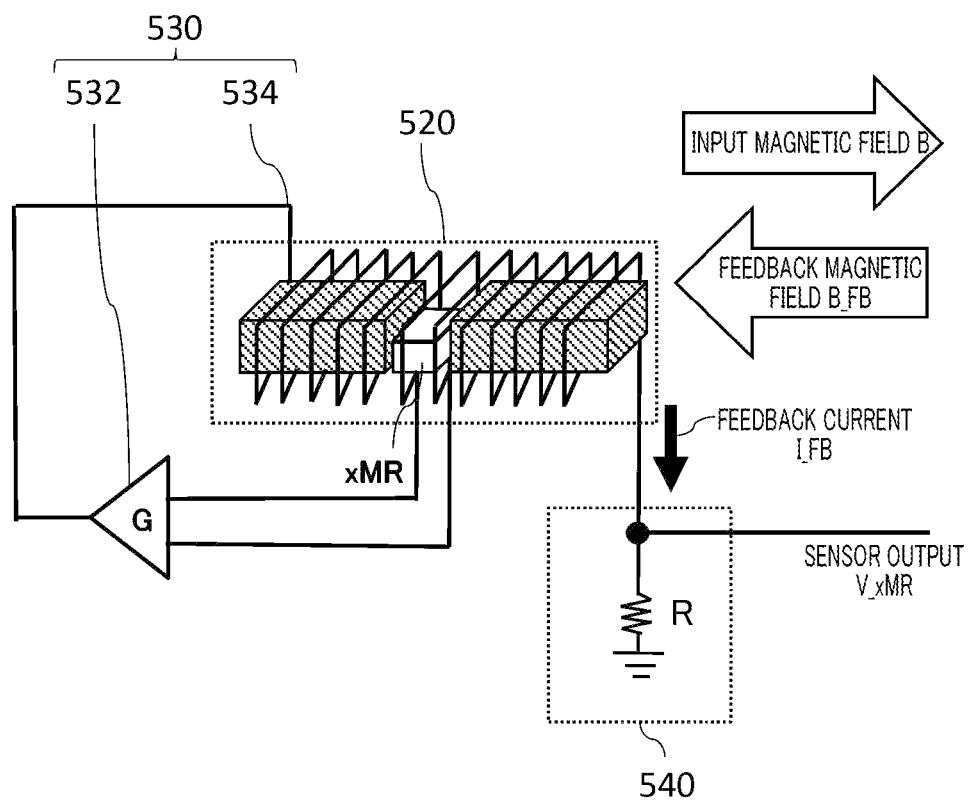
FIG. 5 illustrates an exemplary configuration of a sensor unit 300 according to this embodiment.

FIG. 5 illustrates an exemplary configuration of the sensor unit 300 according to this embodiment. The sensor unit 300 is provided in each of the plurality of magnetic sensor cells 220, and includes the magnetic sensor 520, a magnetic field generation unit 530, and an output unit 540. Note that some of the sensor unit 300, for example, an amplification circuit 532 or the like, may be provided on a side near the sensor data collection unit 230 instead of a side near the magnetic sensor cell 220.

The magnetic sensor 520 includes the magnetoresistive element such as a GMR element or a TMR element similarly to the magnetic sensor explained in FIG. 4. In addition, each of the magnetic sensors 520 includes the magnetoresistive element and two magnetic flux concentrators arranged at both ends of the magnetoresistive element. The magnetoresistive element is arranged at a position sandwiched by the two magnetic flux concentrators. In a case where the positive direction of the magneto-sensitive axis is set to the +X direction, the resistance value of the magnetoresistive element included to form the magnetic sensor 520 may be increased when the magnetic field of the +X direction is input, and the resistance value may be reduced when the magnetic field of the −X direction is input. That is, the magnitude of the input magnetic field B, which is input to the magnetic sensor 520, can be detected by observing the change in the resistance value of the magnetoresistive element included in the magnetic sensor 520. For example, if the magnetic sensitivity of the magnetic sensor 520 is set to S, the detection result of the input magnetic field B of the magnetic sensor 520 can be calculated by S×B. Further, the magnetic sensor 520 is connected to the power source or the like as an example, and outputs the voltage drop according to the change of the resistance value as the detection result of the input magnetic field B. The details of the configuration of the magnetic sensor 520 will be described later.

The magnetic field generation unit 530 generates the feedback magnetic field for reducing the input magnetic field B detected by the magnetic sensor 520 at the magnitude of the output signal output by the output unit 540, and applies the feedback magnetic field to the magnetic sensor 520. The magnetic field generation unit 530 generates, for example, a feedback magnetic field B_FB which has substantially the same absolute value as the input magnetic field B in a reverse direction to the input magnetic field B input to the magnetic sensor 520, and operates to cancel the input magnetic field. The magnetic field generation unit 530 includes the amplification circuit 532 and the feedback coil 534.

The amplification circuit 532 outputs the current according to the detection result of the input magnetic field of the magnetic sensor 520 as a feedback current I_FB. In a case where the magnetoresistive element included in the magnetic sensor 520 is configured by a bridge circuit including at least one magnetoresistive element, the output of the bridge circuit is connected to each of the input terminal pair of the amplification circuit 532. Then, the amplification circuit 532 outputs the current according to the output of the bridge circuit as the feedback current I_FB. The amplification circuit 532 includes, for example, a transconductance amplifier, and outputs the feedback current I_FB according to the output voltage of the magnetic sensor 520. For example, if a voltage-current conversion coefficient of the amplification circuit 532 is set to G, the feedback current I_FB can be calculated by G×S×B.

The feedback coil 534 generates the feedback magnetic field B_FB according to the feedback current I_FB. The feedback coil 534 is wrapped along the axial direction of the magnetic field to be detected by the magnetic sensor 520 so as to surround the magnetoresistive element included in the magnetic sensor 520 and two magnetic flux concentrators arranged at both ends of the magnetoresistive element. It is desirable that the feedback coil 534 generates a uniform feedback magnetic field B_FB over the entire magnetic sensor 520. For example, if the coil coefficient of the feedback coil 534 is set to β, the feedback magnetic field B_FB can be calculated by β×I_FB. Here, the feedback magnetic field B_FB is generated in a direction canceling the input magnetic field B, so that the magnetic field input to the magnetic sensor 520 is reduced to B−B_FB. Therefore, the feedback current I_FB is represented as the following expression.

$$I\_FB = G \times S \times (B - \beta \times I\_FB) \quad \text{[Math. 1]}$$

If (Math. 1) is solved for the feedback current I_FB, the value of the feedback current I_FB in the steady state of the sensor unit 300 can be calculated. If the magnetic sensitivity S of the magnetic sensor 520 and the voltage-current conversion coefficient G of the amplification circuit 532 are sufficiently large, the following expression is calculated from (Math. 1).

$$I\_FB = \frac{G \times S \times B}{1 + G \times S \times \beta} \cong \frac{B}{\beta} \quad \text{[Math. 2]}$$

The output unit 540 outputs an output signal V_xMR according to the feedback current I_FB which flows for the magnetic field generation unit 530 to generate the feedback magnetic field B_FB. The output unit 540 includes, for example, a resistive element having a resistance value R, and outputs the voltage drop generated by the feedback current I_FB flowing in the resistive element as the output signal V_xMR. In this case, the output signal V_xMR is calculated as the following expression (Math. 2).

$$V\_xMR = R \times I\_FB = \frac{R \times B}{\beta} \quad \text{[Math. 3]}$$

As described above, the sensor unit 300 generates the feedback magnetic field for reducing the magnetic field which is input from the outside, so that the magnetic field actually input to the magnetic sensor 520 is reduced. Thereby, the sensor unit 300 uses, for example, a magnetoresistive element which has characteristics of nonlinearity illustrated in FIG. 4 and a narrow operating magnetic field range as the magnetic sensor 520, and can prevent the saturation of the output signal V_xMR even if the absolute value of the input magnetic field B exceeds 1 µT. Next, the input/output characteristics of such a sensor unit 300 will be described.

Figure 6:
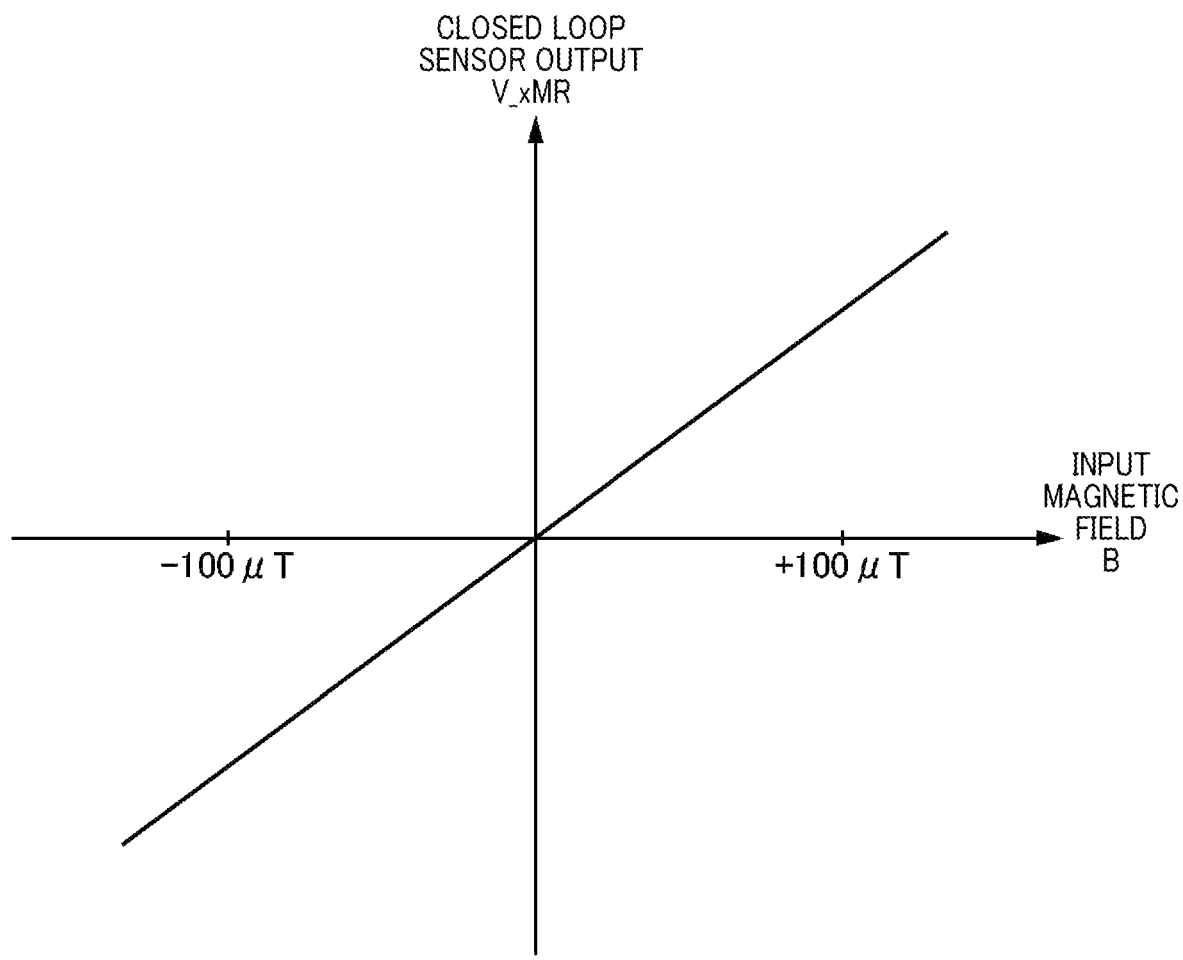
FIG. 6 illustrates an example of the input/output characteristics of the sensor unit 300 according to this embodiment.

FIG. 6 illustrates an example of the input/output characteristics of the sensor unit 300 according to this embodiment. In this drawing, the horizontal axis represents the magnitude B of the input magnetic field which is input to the sensor unit 300, and the vertical axis represents the magnitude V_xMR of the output signal of the sensor unit 300. The sensor unit 300 has a high magnetic sensitivity, and can detect a minute magnetic field having a magnitude of about 10 pT. In addition, the sensor unit 300 can hold, for example, a good linearity of the output signal V_xMR even if the absolute value of the input magnetic field B exceeds 100 pT.

That is, the sensor unit 300 according to this embodiment is configured such that the detection result of the input magnetic field B has linearity in a predetermined range of the input magnetic field B. For example, the absolute value of the input magnetic field B is several hundred pT or less. With the use of such a sensor unit 300, it is possible to easily detect a weak magnetic signal such as a signal of the cardiac magnetic field.

Figure 7:
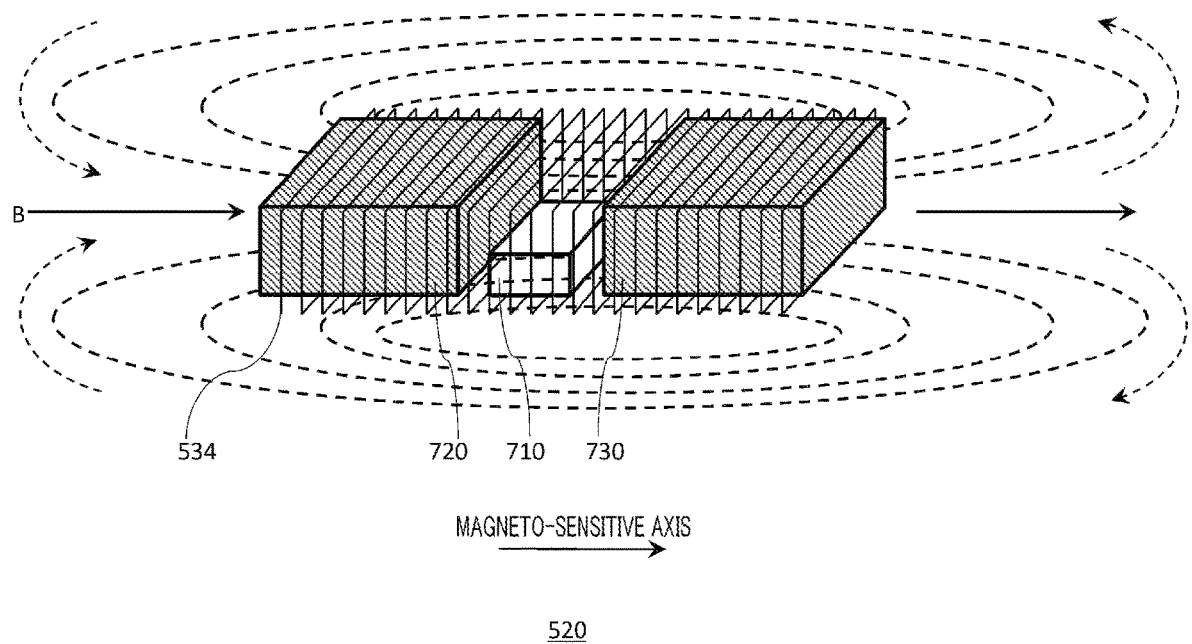
FIG. 7 illustrates an exemplary configuration of a magnetic sensor 520 according to this embodiment.

FIG. 7 illustrates an exemplary configuration of the magnetic sensor 520 according to this embodiment. In this drawing, the magnetic sensor 520 includes a magnetoresistive element 710 and magnetic flux concentrators 720 and 730 arranged at both ends of the magnetoresistive element 710. The magnetic flux concentrators 720 and 730 are arranged at both ends of the magnetoresistive element 710 to sandwich the magnetoresistive element 710 therebetween. In this drawing, the magnetic flux concentrator 720 is provided on the negative side of the magnetoresistive element 710 along the magneto-sensitive axis, and the magnetic flux concentrator 730 is provided on the positive side of the magnetoresistive element 710 along the magneto-sensitive axis. Note that the magneto-sensitive axis may be along the direction of magnetization which is fixed in a magnetization fixed layer for forming the magnetoresistive element 710. In addition, when the magnetic field is input from the negative side toward the positive side of the magneto-sensitive axis, the resistance of the magnetoresistive element 710 may increase or decrease. The magnetic flux concentrators 720 and 730 are formed of a material having a high magnetic permeability such as Permalloy, for example. Then, in a case where the magnetic sensor 520 is configured as illustrated in this drawing, the feedback coil 534 is wrapped along the axial direction of the magnetic field to be detected by the magnetic sensor 520 so as to surround the magnetoresistive element 710 and the cross section of the magnetic flux concentrators 720 and 730 arranged at both ends of the magnetoresistive element 710. In addition, in a case where there are a plurality of magnetoresistive elements 710 in one magnetic sensor 520, the magnetic sensor 520 may include a plurality of sets of the magnetoresistive elements and the magnetic flux concentrators arranged at the both ends thereof. In this case, the feedback coil 534 may be wrapped such that one coil surrounds the set containing the magnetoresistive elements and the magnetic flux concentrators arranged at the both ends thereof.

In such a magnetic sensor 520, when the magnetic field is input from the negative side to the positive side of the magneto-sensitive axis, the magnetic flux concentrators 720 and 730 formed of a material having a high magnetic permeability are magnetized, so that the magnetic flux distribution is generated as indicated with broken lines in this drawing. Then, the magnetic flux generated by the magnetization of the magnetic flux concentrators 720 and 730 passes through the position of the magnetoresistive element 710 sandwiched between the two magnetic flux concentrators 720 and 730. For this reason, the magnetic flux density at the position of the magnetoresistive element 710 can be greatly increased by arranging the magnetic flux concentrators 720 and 730. In addition, as illustrated in this drawing, the sampling point in the space can be clarified by sampling the spatial distribution of the magnetic field using the magnetoresistive element 710 arranged at a narrow position sandwiched by the magnetic flux concentrators 720 and 730.

Figure 8:
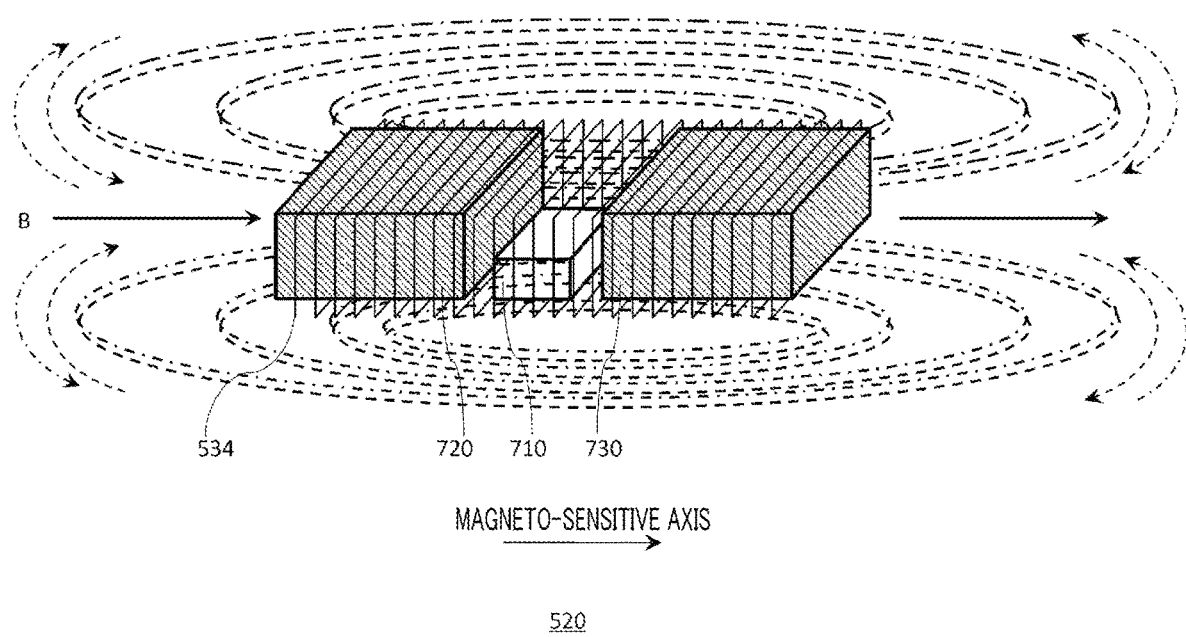
FIG. 8 illustrates a magnetic flux distribution when a feedback magnetic field is generated in the magnetic sensor 520 according to this embodiment.

FIG. 8 illustrates a magnetic flux distribution when the feedback magnetic field is generated in the magnetic sensor 520 according to this embodiment. In FIG. 8, the same symbol is attached to a member having the same function and configuration as those in FIG. 7, and the description will be omitted except for the following differences. In the magnetic sensor 520 according to this embodiment, when a feedback current is supplied to the feedback coil 534, the feedback coil 534 generates the feedback magnetic field, so that the distribution of the magnetic flux is generated as indicated with a dashed line in this drawing. The magnetic flux generated by the feedback magnetic field is input to the magnetoresistive element 710, and is spatially distributed to cancel the spatial distribution of the magnetic field which is magnetically amplified by the magnetic flux concentrators 720 and 730. For this reason, the magnetic sensor 520 can accurately cancel the distribution of the magnetic field at the position of the magnetoresistive element 710 by the feedback magnetic field in a case where the magnetic flux concentrators 720 and 730 are arranged at both ends of the magnetoresistive element 710 as illustrated in this drawing. Therefore, it is possible to realize a sensor having a high linearity between the input magnetic field and the output voltage.

Figure 9:
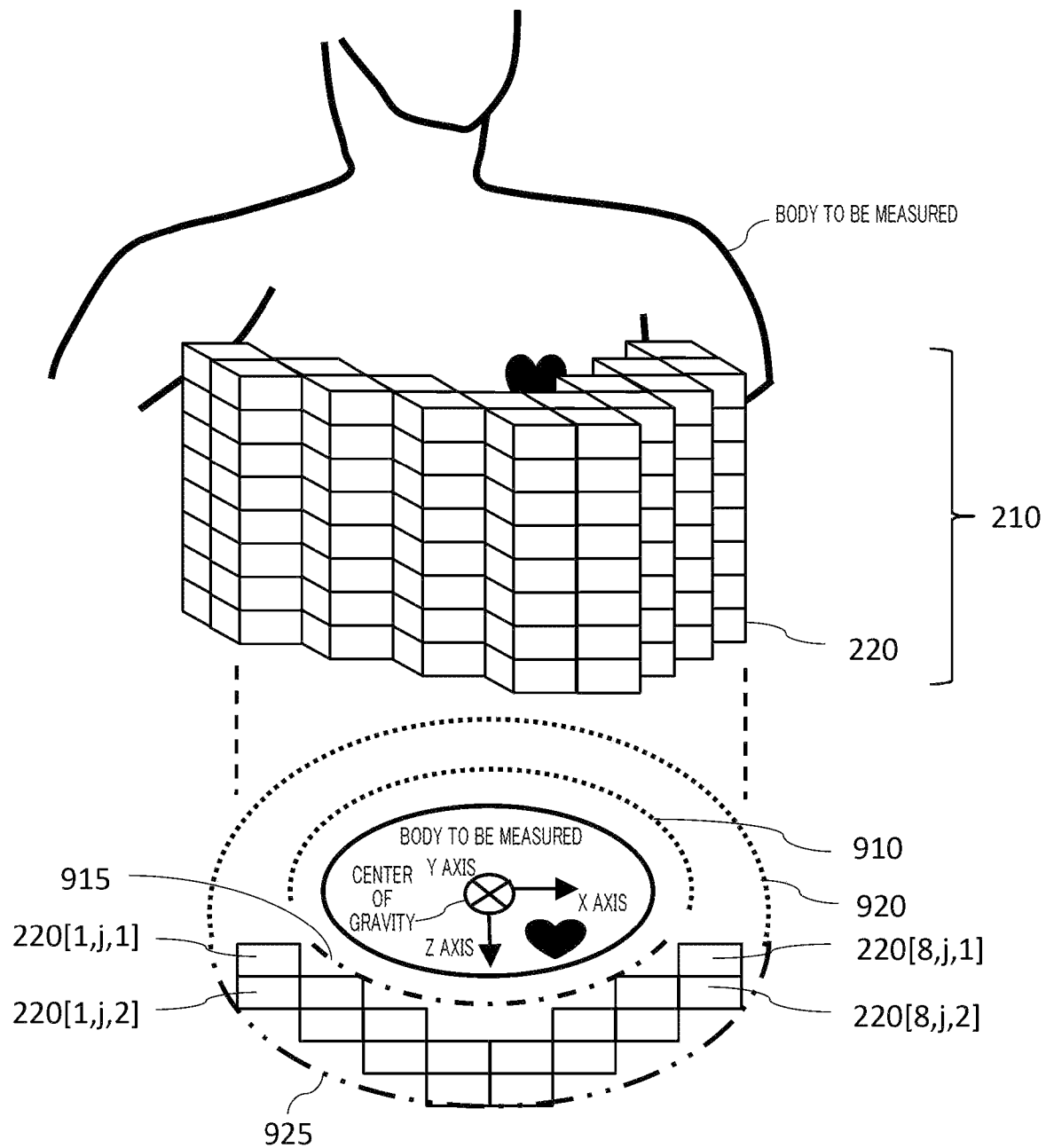
FIG. 9 illustrates an exemplary arrangement of a plurality of magnetic sensor cells 220 in the magnetic sensor array 210 according to this embodiment.

FIG. 9 illustrates an exemplary arrangement of the plurality of magnetic sensor cells 220 in the magnetic sensor array 210 according to this embodiment. In FIG. 2 and FIG. 3, the magnetic sensor array 210 is illustrated in a flat shape for the convenience of explanation. However, as shown in this drawing, in practice, the magnetic sensor array 210 may be configured such that the plurality of magnetic sensor cells 220 are arranged at lattice points between two curved surfaces, each of which is bent in one direction, so as to be three-dimensionally arranged. The two curved surfaces, each of which is bent in one direction, may be, for example, a part of two cylindrical surfaces having the same axis and different diameters from each other. The curvature ratio of the two curved surfaces, each of which is bent in one direction, may be the same, or may be different. As an example, the magnetic sensor array 210 may be configured by three-dimensionally arranging the plurality of magnetic sensor cells 220 in an arc shape in a cross-sectional view.

That is, the plurality of magnetic sensor cells 220 may be arranged in an arc shape in a cross-sectional view along the chest of the object to be measured (subject) about the center of gravity of the object to be measured (subject). At this time, each magnetic sensor cell 220 is arranged at a lattice point between the two curved surfaces, each of which is bent in one direction in the three-dimensional lattice space. Further, here, the lattice points are points in a lattice shape which are provided at predetermined equal intervals in the X direction, the Y direction, and the Z direction, respectively. As an example, each magnetic sensor cell 220 is arranged along the curved surface having convexity in a direction orthogonal to one direction when viewed from any one direction of the X direction, the Y direction, and the Z direction. This drawing illustrates an example in which each magnetic sensor cell 220 is arranged along the curved surface having convexity in a positive direction of the Z axis when viewed from the Y direction. Then, the magnetic sensor array 210 may be formed in a curved shape having convexity in the positive direction of the Z axis, for example, by arranging each magnetic sensor cell 220 at the lattice point in the three-dimensional lattice space such that each vertex of each magnetic sensor cell 220 is arranged in the negative direction of the Z axis as much as possible within a range that does not exceed the predetermined curved surface having convexity in the positive direction of the Z axis.

More specifically, in a cross-sectional view of this drawing, the plurality of magnetic sensor cells 220 on the inside (the negative side of the Z axis), that is, the magnetic sensor cells 220[1, j, 1] to 220[8, j, 1], are arranged outside of the arc displayed with a dashed line of symbol 915 so as to be arranged outside the inscribed circle of the magnetic sensor array 210 indicated by symbol 910. In addition, the plurality of magnetic sensor cells 220 on the outside (the positive side of the Z axis), that is, the magnetic sensor cells 220[1, j, 2] to 220[8, j, 2], are arranged inside the arc displayed with a two-dot chain line of symbol 925 so as to be arranged inside a circumscribed circle of the magnetic sensor array 210 indicated by symbol 920. The center of these inscribed circle and circumscribed circle are common, and matches with the coordinate origin in a signal separation calculation described later.

Thereby, the magnetic sensor array 210 can arrange the sensor unit in many directions as well as one direction facing the heart, and can sense the cardiac magnetic field from many directions. In addition, the magnetic sensor array 210 according to this embodiment can easily change the shape of the magnetic sensor array 210 in order to form the magnetic sensor cell 220 in a cuboid shape as an example. That is, the magnetic sensor array 210 according to this embodiment can employ various shapes that can be configured by arranging the magnetic sensor cell 220 at the lattice point, and the design freedom is high. Therefore, as shown in this drawing, the magnetic sensor array 210 can easily form a curved shape in the three-dimensional space by arranging the plurality of magnetic sensor cells 220 at the lattice points between two curved surfaces, each of which is bent in one direction in the three-dimensional space. Then, the magnetic field measurement device 10 arranges the magnetic sensor array 210 such that the chest of the object to be measured is positioned on the center side of the curved surface, that is, the heart which is a magnetic field source to be measured is positioned on the center side of the curved surface, and measures the magnetic field. Thereby, the magnetic field measurement device 10 can separate a measurement target magnetic field and a disturbance magnetic field with high accuracy by spatially separating the signal space using the measurement data measured at a position near the heart which is a magnetic field source to be measured (described later). Further, at this time, if the curvature of the curved surface is substantially the same as the curvature around the chest of the object to be measured, the magnetic sensor array 210 is preferable because the magnetic field can be measured at a position closer to the heart which is the magnetic field source to be measured.

Figure 10:
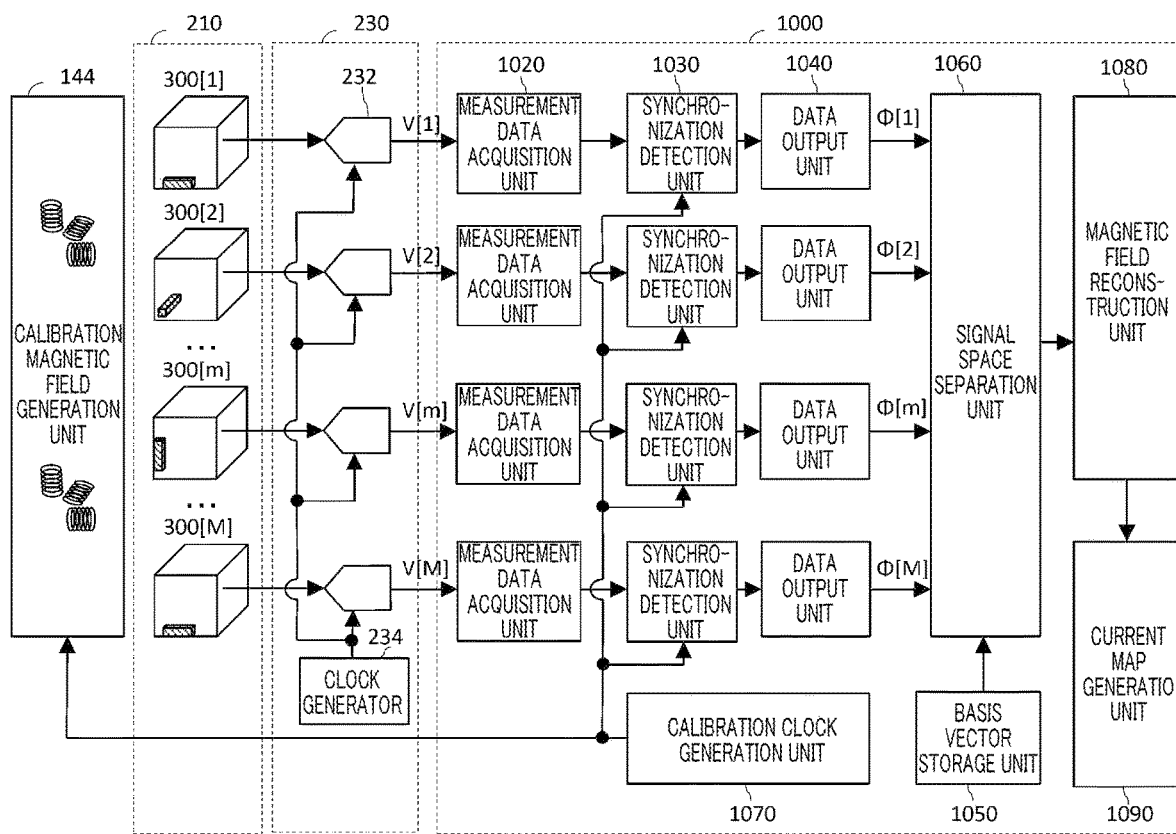
FIG. 10 illustrates the configuration of a calibration magnetic field generation unit 144, a magnetic sensor array 210, a sensor data collection unit 230, and a sensor data processing unit 1000 according to this embodiment.

FIG. 10 illustrates the configuration of the calibration magnetic field generation unit 144, the magnetic sensor array 210, the sensor data collection unit 230, and a sensor data processing unit 1000 according to this embodiment.

The calibration magnetic field generation unit 144 is arranged on a side facing the object to be measured as viewed from the magnetic sensor array 210 when performing calibration. The calibration magnetic field generation unit 144 may have, as described above, a plurality of calibration coils, each of which generates the calibration magnetic field. Then, the calibration magnetic field generation unit 144 may receive a clock signal for calibration, and add the clock signal to each of the plurality of calibration coils so as to generate an AC magnetic field according to the frequency of the clock signal from each of the plurality of calibration coils.

The magnetic sensor array 210 is configured by the plurality of magnetic sensor cells 220, each of which includes at least one sensor unit 300, and can detect the input magnetic field in the three-axial directions of the magnetic sensor array 210 as a whole. This drawing illustrates a case where the magnetic sensor array 210 includes M sensor units 300[1] to 300[M] as an example.

The sensor data collection unit 230 includes a plurality of AD converters 232 and a clock generator 234. The plurality of AD converters 232 are provided corresponding to the plurality of sensor units 300[1] to 300[M] respectively, and convert the analog output signals (V_xMR of FIG. 6) output by the corresponding sensor units 300 into the digital measurement data V[1] to V[M].

The clock generator 234 generates a sampling clock, and supplies the common sampling clock to each of the plurality of AD converters 232. Then, each of the plurality of AD converters 232 performs AD conversion according to the common sampling clock supplied from the clock generator 234. Therefore, all of the plurality of AD converters 232, which performs AD conversion of the outputs of the plurality of sensor units 300[1] to 300[M] provided at different positions, operates in synchronization. Thereby, the plurality of AD converters 232 can synchronously sample the detection results of the plurality of sensor units 300[1] to 300[M] provided in different spaces.

The sensor data processing unit 1000 includes a plurality of measurement data acquisition units 1020, a plurality of synchronization detection units 1030, a plurality of data output units 1040, which are provided corresponding to each of the plurality of sensor units 300[1] to 300[M], and includes a basis vector storage unit 1050, a signal space separation unit 1060, a calibration clock generation unit 1070, a magnetic field reconstruction unit 1080, and a current map generation unit 1090.

The measurement data acquisition unit 1020 acquires the measurement data measured by the magnetic sensor array 210. The measurement data acquisition unit 1020 is connected to each of the plurality of AD converters 232, which are connected to the corresponding sensor unit 300, and acquires the measurement data V[1] to V[M] measured by the plurality of sensor units 300[1] to 300[M] included in the magnetic sensor array 210. Specifically, the measurement data acquisition unit 1020 may be configured using a flip-flop or the like that latches and acquires the digital measurement data V which has been converted into a digital signal by the AD converter 232 at a predetermined timing T. The measurement data acquisition unit 1020 supplies the acquired measurement data V to the synchronization detection unit 1030.

In a case where the measurement target magnetic field is measured, the synchronization detection unit 1030 supplies the measurement data V supplied from the measurement data acquisition unit 1020 to the data output unit 1040 as it is. On the other hand, when performing calibration, the synchronization detection unit 1030 detects the calibration magnetic field which is the AC magnetic field using the frequency signal of the AC magnetic field. As an example, the synchronization detection unit 1030 synchronously detects the calibration magnetic field according to the clock signal for calibration. Then, the synchronization detection unit 1030 extracts a frequency component which is synchronous to the calibration magnetic field, which is an AC magnetic field, from the measurement data V supplied from the measurement data acquisition unit 1020, and supplies the measurement data V related to the extracted frequency component to the data output unit 1040. Here, such a synchronous detection may be performed on software, or may be performed on hardware. In addition, in the above description, the synchronization detection unit 1030 has been described as an example in a case where the synchronous detection is performed to extract the frequency component synchronized with the calibration magnetic field. However, the frequency component synchronized with the calibration magnetic field may be extracted by frequency separation using FFT (a band pass filter for extracting the frequency component synchronized with the calibration magnetic field) or the like.

The data output unit 1040 sets the measurement data V[1] to V[M] supplied from each of the plurality of synchronization detection units 1030 to each of the sensor signal components $\Phi[1]$ to $\Phi[M]$, and supplies a sensor array signal $\Phi$ to the signal space separation unit 1060.

The basis vector storage unit 1050 stores a basis vector which is necessary for the signal space separation unit 1060 to perform signal separation on the sensor array signal $\Phi$, and supplies the basis vector to the signal space separation unit 1060. Further, the basis vector storage unit 1050 may store an optimized basis vector such that a separation error is minimized in a case where the spatial distribution of the calibration magnetic field is signal-separated by the signal space separation unit 1060.

The signal space separation unit 1060 performs signal separation on the spatial distribution of the input magnetic field, which is indicated by the measurement data V [1] to V[M] supplied as each component of the sensor array signal t from the data output unit 1040, using a vector signal, which has the signal output by each of the plurality of magnetic sensors 520 as each signal component, as the basis vector in a case where the magnetic sensor array 210 detects the magnetic field having a spatial distribution of the orthonormal function. That is, the signal space separation unit 1060 performs signal separation on the spatial distribution of the input magnetic field indicated by the measurement data V[1]

to V[M] based on a basis vector calculated from the orthonormal function and the position and magnetic sensitivity of each magnetic sensor 520 of the magnetic sensor array 210. At this time, the signal space separation unit 1060 acquires a basis vector necessary for the signal separation from the basis vector storage unit 1050. Then, the signal space separation unit 1060 performs signal separation on the spatial distribution of the magnetic field indicated by the measurement data V[1] to V[M] into the measurement target magnetic field (signal source space signal) and the disturbance magnetic field (disturbance space signal) using the basis vector acquired from the basis vector storage unit 1050. The signal space separation unit 1060 supplies the signal separation result to the magnetic field reconstruction unit 1080. This will be described later.

The calibration clock generation unit 1070 generates a clock signal for generating an AC calibration magnetic field when performing calibration. Then, the calibration clock generation unit 1070 supplies the generated clock signal to the calibration magnetic field generation unit 144 and each of the plurality of synchronization detection units 1030. Accordingly, the calibration magnetic field generation unit 144 adds the clock signal to each of the plurality of calibration coils to generate the AC magnetic field according to the frequency of the clock signal from each of the plurality of calibration coils. In addition, the plurality of synchronization detection units 1030 detects the respective AC calibration magnetic field, which is generated by the calibration magnetic field generation unit 144, according to the clock signal. Further, in the above description, a case where the calibration clock generation unit 1070 is provided in the sensor data processing unit 1000 has been described as an example. However, the calibration clock generation unit 1070 may be configured, for example, in the calibration magnetic field generation unit 144.

The magnetic field reconstruction unit 1080 reconstructs the magnetic field component orthogonal to the virtual sensor array plane with respect to one or more positions on the virtual sensor array plane, which is a plane designated in the three-dimensional space, using the measurement data V[1] to V[M] supplied as each component of the sensor array signal Φ. At this time, the magnetic field reconstruction unit 1080 may reconstruct the magnetic field of the measurement target magnetic field component, from which the disturbance magnetic field component is separated, with respect to one or more positions on the virtual sensor array plane based on the result obtained by the signal separation of the signal space separation unit 1060. The magnetic field reconstruction unit 1080 supplies the information related to the reconstructed magnetic field to the current map generation unit 1090. This will be described later.

The current map generation unit 1090 generates a current map, in which the state of the active current due to the electrical activity of the object to be measured is projected onto the virtual sensor array plane, using the magnetic field which is reconstructed with respect to a plurality of positions on the virtual sensor array plane. At this time, the current map generation unit 1090 may generate a current arrow map showing current vectors at the plurality of positions based on a difference between the magnetic field reconstructed with respect to each of the plurality of positions on the virtual sensor array plane and the magnetic field reconstructed with respect to the adjacent positions. The current map generation unit 1090 outputs the generated current map by displaying, printing, or the like. This will be described in detail using formulas.

Figure 11:
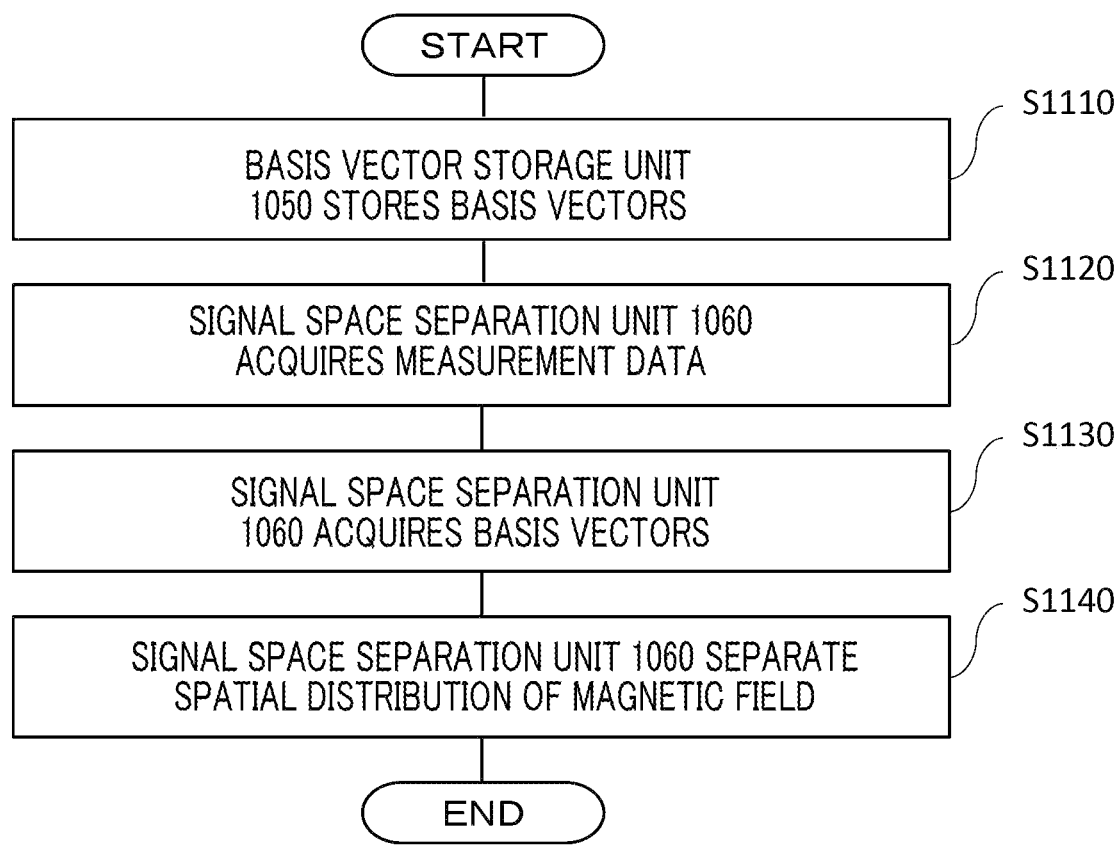
FIG. 11 illustrates a flow in which the magnetic field measurement device 10 according to this embodiment performs signal separation on a spatial distribution of the magnetic field.

FIG. 11 illustrates a flow in which the magnetic field measurement device 10 according to this embodiment performs signal separation on the spatial distribution of the magnetic field. In Step 1110, the basis vector storage unit 1050 stores the basis vector. As an example, the basis vector storage unit 1050 may store a signal vector, which is predetermined from a simulation result on assumption that the magnetic sensor array 210 is ideally manufactured without errors in each sensor, as an initial basis vector. In addition, the basis vector storage unit 1050 may store an optimized basis vector such that a separation error is minimized in a case where the spatial distribution of the calibration magnetic field is signal-separated by the signal space separation unit 1060.

Next, in Step 1120, the signal space separation unit 1060 acquires the sensor array signal Φ measured by the magnetic sensor array 210, that is, the measurement data V[1] to V[M] from the data output unit 1040.

In addition, in Step 1130, the signal space separation unit 1060 acquires the signal vector, which is stored by the basis vector storage unit 1050 as the basis vector in Step 1110, from the basis vector storage unit 1050. Further, in this flow, either of Step 1120 and Step 1130 may be performed first.

In Step 1140, the signal space separation unit 1060 performs series expansion on the spatial distribution of the magnetic field indicated by the measurement data V [1] to V[M] acquired in Step 1120 using the signal vector acquired in Step 1130 as a basis vector. Then, the signal space separation unit 1060 performs signal separation on the spatial distribution of the magnetic field into the measurement target magnetic field and the disturbance magnetic field from the vector obtained by the series expansion. That is, the signal space separation unit 1060 performs signal separation on the spatial distribution of the input magnetic field, which is indicated by the measurement data V[1] to V[M], using a vector signal, which has the signal output by each of the magnetic sensors 520 as each signal component, as the basis vector in a case where the magnetic sensor array 210 detects the magnetic field having a spatial distribution of the orthonormal function. That is, the signal space separation unit 1060 performs signal separation on the spatial distribution of the input magnetic field indicated by the measurement data V Hi to V[M] based on a basis vector calculated from the orthonormal function and the position and magnetic sensitivity of each magnetic sensor 520 of the magnetic sensor array 210. Here, the orthonormal function may be a spherical harmonic function. In addition, at the time of signal separation, the signal space separation unit 1060 calculates the coefficient of the basis vector by the least square method. Hereinafter, this will be described in detail.

Regarding the position where each sensor of the magnetic sensor array 210 is arranged, when current i(r)=0 at the position of a position vector r indicating the position from the coordinate origin, an electrostatic magnetic field B(r) is obtained as a space gradient of a potential V(r) using the potential V(r) satisfying the Laplace's equation Δ·V(r)=0, as shown in the following expression. Here, Δ represents Laplacian, μ represents magnetic permeability, and ∇ represents an operator indicating a vector differential operation.

$$B(r) = -\mu \cdot \nabla \cdot V(r) \qquad \text{[Math. 4]}$$

Then, the solution of the Laplace's equation generally has a solution in the form of a series expansion using a spherical harmonic function $Y_{l,m}(\theta, \varphi)$, which is an orthonormal function. Therefore, the potential V(r) can be represented as the following expression. Herein, |r| represents the absolute value of the position vector r (the distance from the coordinate origin), θ and φ represent two deviations in the spherical coordinates, l represents an azimuthal quantum number, m represents a magnetic quantum number, α and β represent multipole moments, and Lin and Lout represent the number of series for each of the front space and the rear space of the magnetic sensor array 210 when viewed from the object to be measured. The azimuthal quantum number l is a positive integer, and the magnetic quantum number m is an integer from −l to +l. That is, for example, when l is 1, m is −1, 0, and 1. For example, when l is 2, m is −2, −1, 0, 1, and 2. Further, since a single magnetic pole does not exist in the magnetic field, the azimuthal quantum number l in (Math. 5) starts from 1 instead of 0. The first term in (Math. 5) is a term inversely proportional to the distance from the coordinate origin, and indicates the potential existing in the front space of the magnetic sensor array 210 when viewed from the coordinate origin. In addition, the second term in (Math. 5) is a term proportional to the distance from the coordinate origin, and indicates the potential existing in the rear space of the magnetic sensor array 210 when viewed from the coordinate origin.

$$V(r) = \sum_{l=1}^{Lin} \sum_{m=-l}^{l} \alpha_{l,m} \cdot \left( \frac{1}{|r|^{l+1}} \cdot Y_{l,m}(\theta, \varphi) \right) + \sum_{l=1}^{Lout} \sum_{m=-l}^{l} \beta_{l,m} \cdot (|r|^l \cdot Y_{l,m}(\theta, \varphi))$$

[Math. 5]

Therefore, according to (Math. 4) and (Math. 5), the electrostatic magnetic field B(r) can be represented by the following expression. Here, the first term in (Math. 6) represents a magnetic field source existing in the front space of the magnetic sensor array 210 when viewed from the object to be measured, that is, for example, the cardiac magnetic field (the measurement target magnetic field) creating the electrical activity of the heart. In addition, the second term in (Math. 6) represents the disturbance magnetic field created by the magnetic field source existing in the rear space of the magnetic sensor array 210 when viewed from the object to be measured.

$$B(r) = -\mu \sum_{l=1}^{Lin} \sum_{m=-l}^{l} \alpha_{l,m} \cdot \nabla \left( \frac{1}{|r|^{l+1}} \cdot Y_{l,m}(\theta, \varphi) \right) - \mu \sum_{l=1}^{Lout} \sum_{m=-l}^{l} \beta_{l,m} \cdot \nabla (|r|^l \cdot Y_{l,m}(\theta, \varphi))$$

[Math. 6]

In a case where the solution of the Laplace's equation is represented in the form of series expansion using a spherical harmonic function, the general solution is an infinite series. However, it is said that a series of about 10 terms is sufficient for actual representing as long as the SNR (signal noise ratio, that is, a ratio of the signals of the disturbance magnetic field and the measurement target magnetic field for the sensor noise) sufficient for measuring a biological magnetic field is obtained. In addition, it is said that approximately Lin=8 and Lout=3 may be used for the series of signal space separation in a magnetoencephalograph. Therefore, also in this embodiment, the case of Lin=8 and Lout=3 will be described as an example. However, the values of Lin and Lout are not limited to these, and may be any numerical value with which the disturbance magnetic field is sufficiently suppressed, and only the measurement target magnetic field is calculated.

Here, the sensor array signal Φ is an M-dimensional vector, and each signal component of the vector is the inner product of a magnetic field vector B(r[m]) in the position vector r[m] where the magnetic sensor 520 of each sensor unit 300 is arranged and the magnetic sensitivity vector S[m] of each magnetic sensor 520. Therefore, in a case where each magnetic sensor 520 has a magnetic sensitivity vector S[m]=(S[m], x, S[m], y, S[m], z), the sensor array signal Φ is represented by the following expression.

$$\begin{pmatrix} \phi[1] \\ \phi[2] \\ \vdots \\ \phi[m] \\ \vdots \\ \phi[M] \end{pmatrix} = \begin{pmatrix} \overrightarrow{S[1]} \cdot \overrightarrow{B(r[1])} \\ \overrightarrow{S[2]} \cdot \overrightarrow{B(r[2])} \\ \vdots \\ \overrightarrow{S[m]} \cdot \overrightarrow{B(r[m])} \\ \vdots \\ \overrightarrow{S[M]} \cdot \overrightarrow{B(r[M])} \end{pmatrix}$$

[Math. 7]

That is, each sensor signal component Φ[m] is represented by the following expression.

$$\phi[m] = S[m], x \cdot Bx(r[m]) + S[m], y \cdot By(r[m]) + S[m], z \cdot Bz(r[m])$$

[Math. 8]

$$m \in \{1, 2, \ldots, M\}$$

Therefore, the basis vectors $a_{l,m}$ and $b_{l,m}$ are defined as the following expression.

$$a_{l,m} = -\mu \begin{bmatrix} S[1] \cdot \nabla \left( \frac{1}{r[1]^{l+1}} Y_{l,m}(\theta[1], \varphi[1]) \right) \\ S[2] \cdot \nabla \left( \frac{1}{r[1]^{l+1}} Y_{l,m}(\theta[2], \varphi[2]) \right) \\ \vdots \\ S[m] \cdot \nabla \left( \frac{1}{r[1]^{l+1}} Y_{l,m}(\theta[m], \varphi[m]) \right) \\ \vdots \\ S[1] \cdot \nabla \left( \frac{1}{r[M]^{l+1}} Y_{l,m}(\theta[M], \varphi[M]) \right) \end{bmatrix}$$

[Math. 9]

$$b_{l,m} = -\mu \begin{bmatrix} S[1] \cdot \nabla (r[m]^l Y_{l,m}(\theta[1], \varphi[1])) \\ S[2] \cdot \nabla (r[m]^l Y_{l,m}(\theta[2], \varphi[2])) \\ \vdots \\ S[m] \cdot \nabla (r[m]^l Y_{l,m}(\theta[m], \varphi[m])) \\ \vdots \\ S[M] \cdot \nabla (r[m]^l Y_{l,m}(\theta[M], \varphi[M])) \end{bmatrix}$$

Here, A, B, Xin, and Xout each are defined as follows. That is, A is defined as a vector of the total Lin·(Lin+2) array in which each vector a when an integer m=−l to l is taken in each l (l=1 to Lin) is sequentially arranged in a row. In addition, B is defined as a vector of the total Lout·(Lout+2) array in which each vector b when an integer m=−l to l is taken in each l (l=1 to L=Lout) is sequentially arranged in a row. In addition, Xin is defined as a vector of the total Lin·(Lin+2) array obtained by transposing a vector in which each multipole moment α when an integer m=−l to l is taken in each l (l=1 to L=Lin) is sequentially arranged in a row. In addition, Xout is defined as a vector of the total Lout·(Lout+2) array obtained by transposing a vector in which each multipole moment β when an integer m=−l to l is taken in each l (l=1 to l=Lout) is sequentially arranged in a row.

$$A = [a_{1,-1}\ a_{1,0}\ a_{1,+1}\ \ldots\ a_{Lin,Lin}]$$

$$B = [b_{1,-1}\ b_{1,0}\ b_{1,+1}\ \ldots\ b_{Lout,Lout}]$$

$$Xin = [\alpha_{1,-1}\ \alpha_{1,0}\ \alpha_{1,+1}\ \ldots\ \alpha_{Lin,Lin}]^t$$

$$Xout = [\beta_{1,-1}\ \beta_{1,0}\ \beta_{1,+1}\ \ldots\ \beta_{Lout,Lout}]^t \quad \text{[Math. 10]}$$

Then, the sensor array signal Φ can be represented in the form of inner product of the basis vector array [AB] and a column vector X as shown in the following expression. Here, the basis vector array [AB] represents a basis vector, and is acquired in Step 1130 by the signal space separation unit 1060 from the basis vector storage unit 1050 for example. In addition, the column vector X indicates a coefficient related to the basis vector.

$$\Phi = [A\ B] \cdot X = [A\ B] \begin{bmatrix} Xin \\ Xout \end{bmatrix} \quad \text{[Math. 11]}$$

The signal space separation unit 1060 uses the following expression to determine a column vector ˆX (here, "ˆX" indicates the left side in (Math. 12), and means the hat of X (estimated value)) satisfying Φ=[A B]·X with the least square method based on the model formula obtained by (Math. 11) in Step 1140.

$$\hat{X} = \begin{bmatrix} \widehat{Xin} \\ \widehat{Xout} \end{bmatrix} = [A\ B]^\dagger \cdot \Phi = ([A\ B]^t \cdot [A\ B]^{-1}) \cdot [A\ B]^t \cdot \Phi \quad \text{[Math. 12]}$$

Therefore, the signal space separation unit 1060 can represent the hat ˆΦ of the sensor array signal as an M-dimensional vector of the least square solution by the following expression. Thereby, the signal space separation unit 1060 can solve the spatial distribution of the magnetic field in Step 1140.

$$\hat{\phi} = [A\ B] \cdot \{[A\ B]^\dagger \cdot \Phi\} = [A\ B] \cdot \{([A\ B]^t \cdot [A\ B])^{-1} \cdot [A\ B]^t \cdot \Phi\} \quad \text{[Math. 13]}$$

Thereby, according to the magnetic field measurement device 10 of this embodiment, the spatial distribution of the magnetic field indicated by the measurement data V [1] to V[M] measured using the magnetic sensor array 210, which have the plurality of magnetic sensor cells 220 and can detect the input magnetic field in the three-axial directions, can be signal-separated into the measurement target magnetic field component ˆXin·A and the disturbance magnetic field component ˆXout·B. According to the magnetic field measurement device 10 of this embodiment, each of the plurality of sensor units 300 has the magnetic flux concentrator. Therefore, the magnetic sensitivity of the sensor unit 300 can be increased, the spatial sampling point can also be clarified, and the affinity with the signal space separation technology can be further increased.

Figure 12:
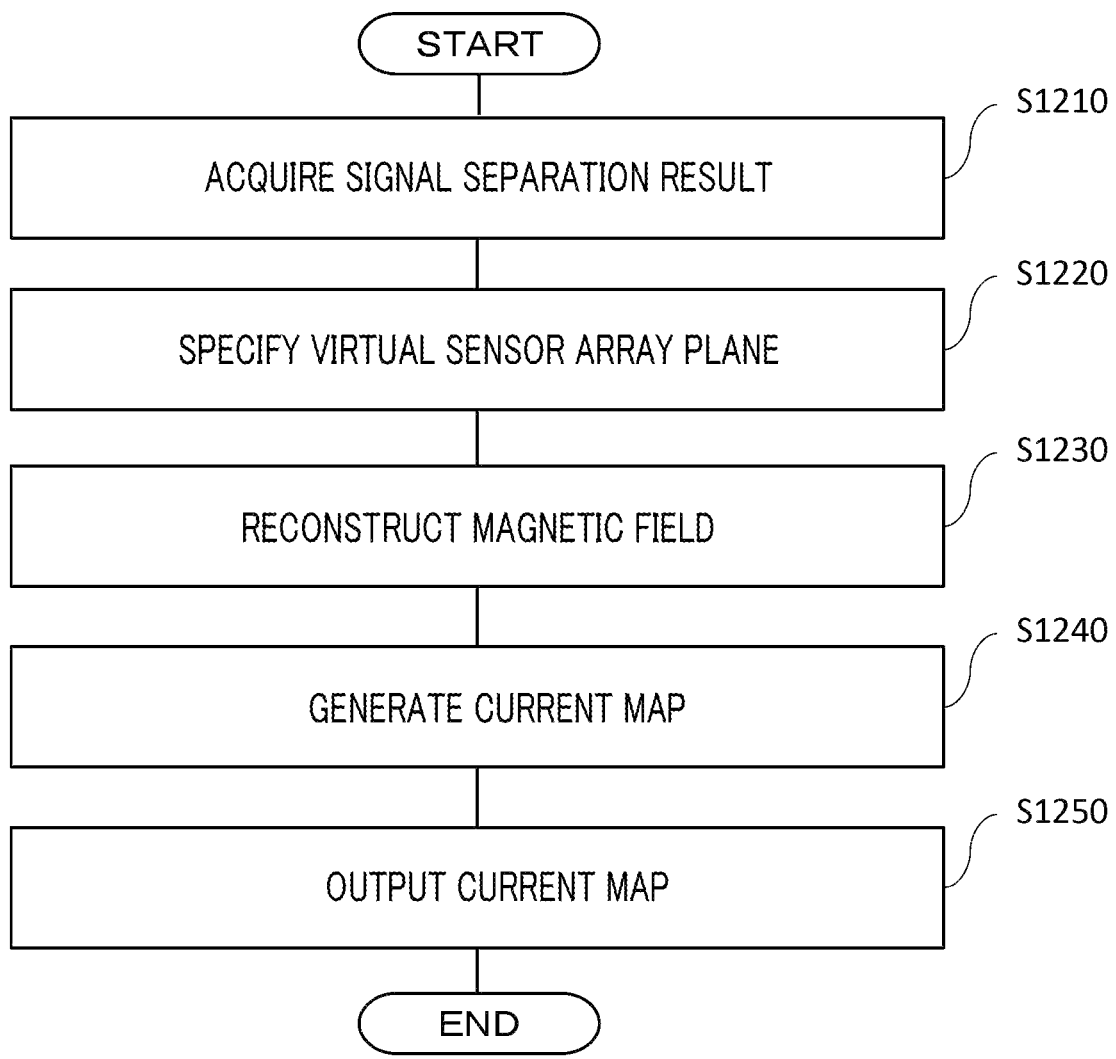
FIG. 12 illustrates a flow in which the magnetic field measurement device 10 according to this embodiment reconstructs the magnetic field to generate a current map.

FIG. 12 illustrates a flow in which the magnetic field measurement device 10 according to this embodiment reconstructs the magnetic field to generate the current map. In Step 1210, the magnetic field measurement device 10 acquires a signal separation result. As an example, the magnetic field reconstruction unit 1080 acquires the information related to the signal separation result obtained by the signal space separation unit 1060 in the flow of FIG. 11 from the signal space separation unit 1060. For example, the magnetic field reconstruction unit 1080 acquires the information related to the column vector ˆX determined by the signal space separation unit 1060 from the signal space separation unit 1060 as the information related to the signal separation result.

In Step 1220, the magnetic field measurement device 10 specifies the virtual sensor array plane. The virtual sensor array plane is a virtual plane specified in the three-dimensional space which may not have a sensor as an entity. The magnetic field measurement device 10 may accept, for example, a user's input, and may specify the virtual sensor array plane based on the user's input. Instead, the magnetic field measurement device 10 may automatically specify, for example, a predetermined plane as the virtual sensor array plane based on a relative positional relationship from the magnetic sensor array 210. In addition, the magnetic field measurement device 10 may automatically specify the virtual sensor array plane based on an image obtained by capturing the object to be measured (subject). In a case where the magnetic field measurement device 10 measures the cardiac magnetic field to be measured which is the magnetic field generated by the electrical activity of the heart, the virtual sensor array plane may be specified directly above (front surface) the chest of the object to be measured. Before this, the virtual sensor array plane will be described as being specified in the plane parallel to the XY plane directly above (front surface) the chest of the object to be measured.

In Step 1230, the magnetic field measurement device 10 reconstructs the magnetic field. As an example, the magnetic field reconstruction unit 1080 reconstructs the magnetic field of the component orthogonal to the virtual sensor array plane with respect to one or more positions on the virtual sensor array plane, which is the plane specified in the three-dimensional space, using the measurement data. For example, the magnetic field reconstruction unit 1080 reconstructs the magnetic field with respect to a plurality of positions (for example, 8 positions in the X axis direction×8 positions in the Y axis direction=total 64 positions), which are arranged at equal intervals (for example, the intervals of 2.5 cm in the X axis direction, and 2.5 cm in the Y axis direction) in a lattice shape in the virtual sensor array plane specified in Step 1220, based on the signal separation result acquired in Step 1210. That is, the magnetic field measurement device 10 reconstructs the magnetic field using the following expression with respect to each of the plurality of position vectors r[i, j, k] (in a three-dimensional polar coordinate display, (r[i, j, k], θ[i, j, k], φ[i, j, k]); 1≤i≤8, 1≤j≤8, k=1) on the virtual sensor array plane.

$$B_{Reconstruct}(r[i, j, k]) = -\mu \sum_{l=1}^{Lin} \sum_{m=-l}^{l} \widehat{Xin} \quad \text{[Math. 14]}$$

$$(l, m) \cdot \nabla \left( \frac{1}{r[i, j, k]^{l+1}} \cdot Y_{l,m}(\theta[i, j, k], \varphi[i, j, k]) \right) -$$

-continued $$\mu \sum_{l=1}^{Lin} \sum_{m=-l}^{l} \overline{X_{out}}(l, m) \cdot$$

$$\nabla(r[i, j, k]^l \cdot Y_{l,m}(\theta[i, j, k], \varphi[i, j, k]))$$

Here, the first term in (Math. 14) represents the measurement target magnetic field component, and the second term represents the disturbance magnetic field component. Therefore, the magnetic field reconstruction unit 1080 extracts only the first term in (Math. 14), and acquires the magnetic field reconstructed with respect to one or more positions of the virtual sensor array plane. In this way, the magnetic field reconstruction unit 1080 reconstructs the magnetic field of the measurement target magnetic field component, from which the disturbance magnetic field component is separated, with respect to one or more positions on the virtual sensor array plane based on the result obtained by the signal separation. Further, at this time, the reconstructed magnetic field includes the three-axis components including the X axis component, the Y axis component, and the Z axis component. Therefore, the magnetic field reconstruction unit 1080 supplies only the Z axis component Bz among the reconstructed three-axis components to the current map generation unit 1090.

In Step 1240, the magnetic field measurement device 10 generates a current map. As an example, the current map generation unit 1090 generates a current map, in which the state of the active current due to the electrical activity of the object to be measured is projected onto the virtual sensor array plane, using the magnetic field which is reconstructed with respect to a plurality of positions on the virtual sensor array plane in Step 1230. More specifically, the current map generation unit 1090 generates a current arrow map showing current vectors at the plurality of positions based on a difference between the magnetic field reconstructed with respect to each of the plurality of positions on the virtual sensor array plane and the magnetic field reconstructed with respect to the adjacent positions, using the following expression (2≤i≤8 and 2≤j≤8).

$$Ix = \Delta Bz/\Delta x = Bz[i,j] - Bz[i-1,j]$$

$$Iy = \Delta Bz/\Delta y = Bz[i,j] - Bz[i,j-1] \quad \text{[Math. 15]}$$

In Step 1250, the magnetic field measurement device 10 outputs the current map. As an example, the current map generation unit 1090 outputs the current map generated in Step 1240 by displaying, printing, or the like. Then, the magnetic field measurement device 10 ends the flow.

Figure 13:
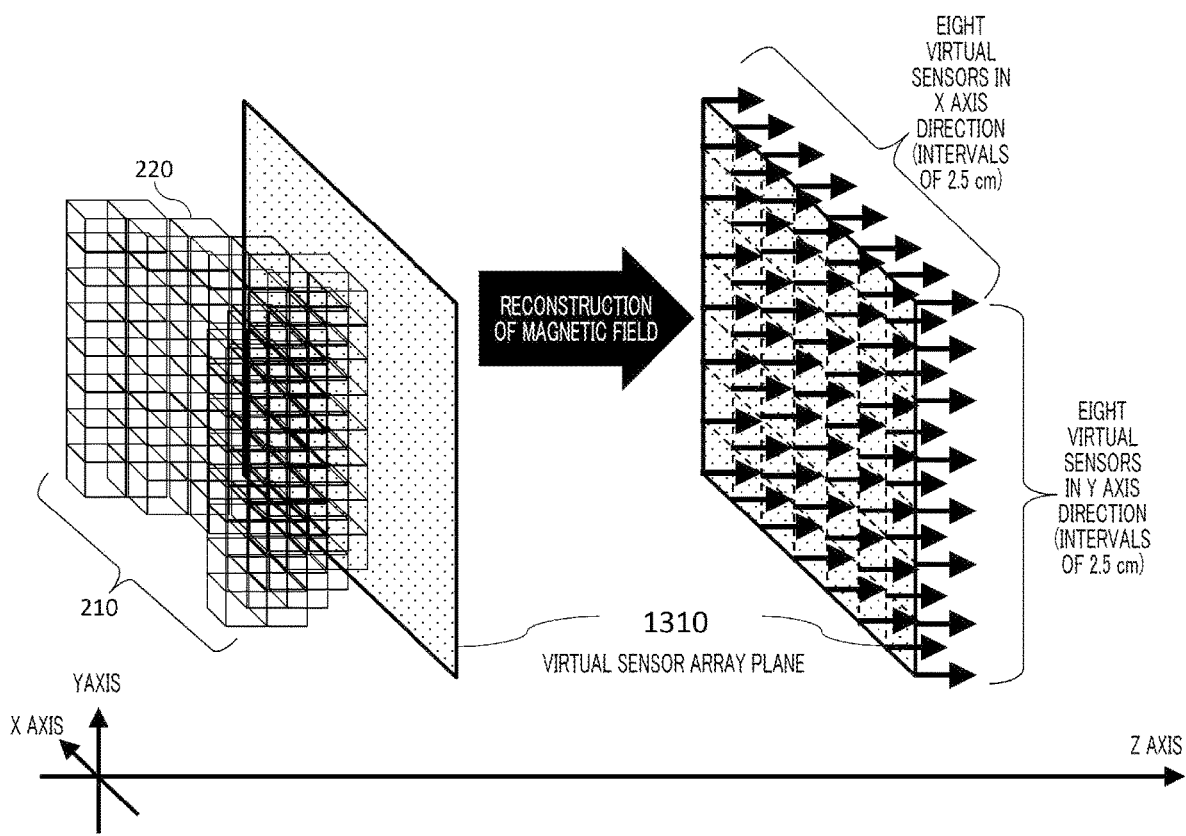
FIG. 13 illustrates an example of the magnetic field which is reconstructed at one or more positions on a virtual sensor array plane by the magnetic field measurement device 10 according to this embodiment.

FIG. 13 illustrates an example of the magnetic field which is reconstructed at one or more positions on the virtual sensor array plane by the magnetic field measurement device 10 according to this embodiment. As illustrated on the left of this drawing, the magnetic field measurement device 10 according to this embodiment measures the magnetic field using the magnetic sensor array 210 which includes the plurality of magnetic sensor cells 220, each of which includes the magnetic sensor 520 and the output unit 540 for outputting the output signal, are arranged at lattice points between two curved surfaces, each of which is bent in one direction, so as to be three-dimensionally arranged, and is capable of detecting the input magnetic field in the three-axial directions. In addition, the magnetic field measurement device 10 specifies a virtual sensor array plane 1310 which is a plane specified in the three-dimensional space. Such a virtual sensor array plane 1310 is a virtual plane which may not have a sensor as an entity. In this drawing, the virtual sensor array plane 1310 is specified to a plane parallel to the XY plane directly above (front surface) of the chest of the object to be measured. Then, the magnetic field measurement device 10 reconstructs the magnetic field of the component orthogonal to the virtual sensor array plane with respect to one or more positions on the virtual sensor array plane 1310, for example, according to the flow of FIG. 11 and FIG. 12, using the measurement data measured by the three-dimensional magnetic sensor array 210 which can detect the input magnetic field in such three-axial directions. As an example, in the magnetic field measurement device 10, as illustrated on the right of this drawing, 8 virtual sensors are arranged at equal intervals (2.5 cm) in the X axis direction on the virtual sensor array plane 1310 which is a plane parallel to the XY plane, and 8 virtual sensors are arranged at equal intervals (2.5 cm) in the Y axis direction, so that the magnetic field of the Z axis component is reconstructed at the positions of 8 virtual sensors in the X axis direction×8 virtual sensors in the Y axis direction=64 virtual sensors in total.

Figure 14:
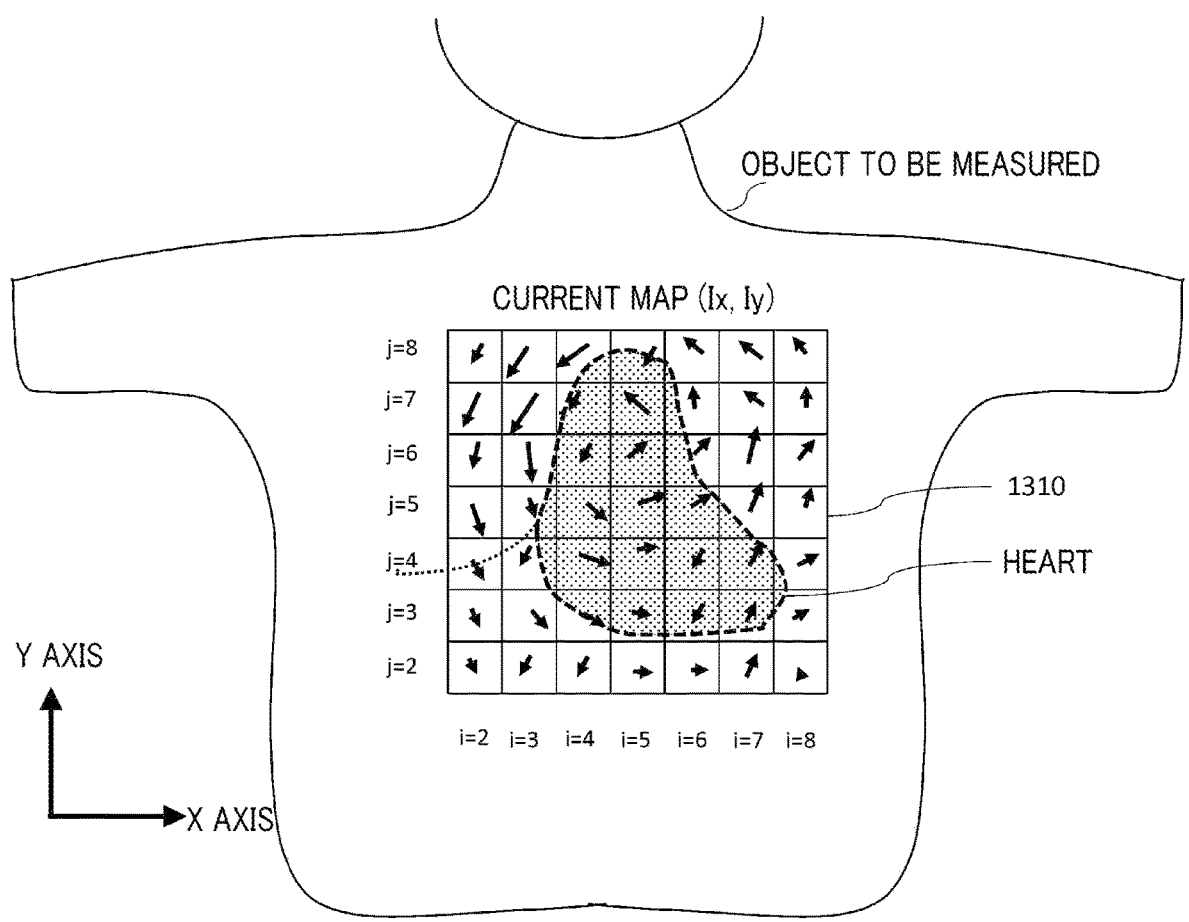
FIG. 14 illustrates an example of a current map which is generated by the magnetic field measurement device 10 according to this embodiment.

FIG. 14 illustrates an example of the current map generated by the magnetic field measurement device 10 according to this embodiment. The magnetic field measurement device 10 according to this embodiment uses, as illustrated in FIG. 13, the magnetic field reconstructed at a plurality of positions on the virtual sensor array plane 1310 so as to generate, for example, a current map in which the state of the active current due to the electrical activity of the object to be measured is projected onto the virtual sensor array plane 1310 by (Math. 15). This drawing illustrates, as an example, a case where the magnetic field measurement device 10 generates a current arrow map showing the vectors of the active current due to the electric activity of the heart in (8−1) places in the X axis direction× (8−1) places in the Y axis direction=49 places in total on the virtual sensor array plane 1310. The magnetic field measurement device 10 according to this embodiment may display the current map thus generated to be overlapped with various images. For example, the magnetic field measurement device 10 can display the generated current map to be overlapped with an X ray image or a CT image taken of the heart. At this time, a magnetic marker (minute coil) for positioning is arranged in the chest when measuring the cardiac magnetic field by the magnetic field measurement device 10 according to this embodiment. In addition, a positioning marker is also arranged when taking an X ray image or a CT image. Then, the magnetic field measurement device 10 may display the current map to be overlapped with various images by positioning them using these markers. Thereby, the magnetic field measurement device 10 can provide more useful diagnostic information.

In this way, the magnetic field measurement device 10 according to this embodiment reconstructs the magnetic field on the virtual sensor array plane using the measurement data measured by the three-dimensional magnetic sensor array 210 which can detect the input magnetic field in the three-axial directions. Thereby, according to the magnetic field measurement device 10 of this embodiment, for example, the magnetic field can be measured and reproduced with more accuracy by sensing from many directions compared to a case where the magnetic field is measured using a sensor array in which sensors for measuring only the magnetic field of one-axis component (perpendicular component) are arranged in a flat shape. In addition, the magnetic field measurement device 10 according to this embodiment generates a current map such as the current arrow map using the magnetic field reproduced with such a high accuracy. Thereby, according to the magnetic field measurement device 10 of this embodiment, it is possible to provide a current map with more high accuracy. In addition, according to the magnetic field measurement device 10 of this embodiment, the spatial distribution of the input magnetic field indicated by the measurement data is signal-separated, and the magnetic field of the measurement target magnetic field component from which the disturbance magnetic field component is separated is reconstructed. Thereby, according to the magnetic field measurement device 10 of this embodiment, the environmental magnetic field can be cancelled, and the measurement of the measurement target magnetic field can be realized without a magnetically shielded room.

Figure 15:
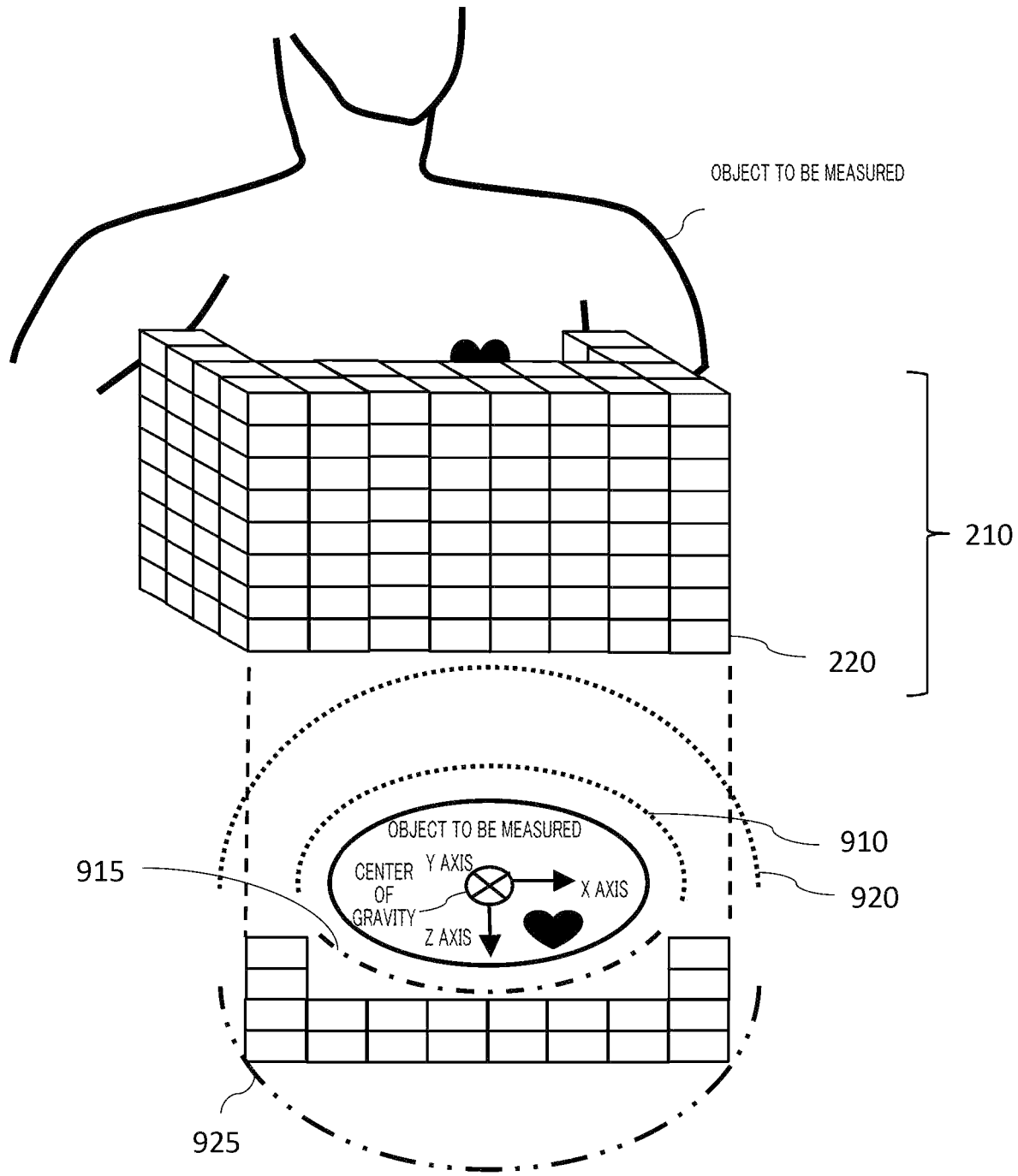
FIG. 15 illustrates an exemplary arrangement of a plurality of magnetic sensor cells 220 in the magnetic sensor array 210 according to a modification of this embodiment.

FIG. 15 illustrates an exemplary arrangement of the plurality of magnetic sensor cells 220 in the magnetic sensor array 210 according to a modification of this embodiment. In FIG. 15, the same symbol is attached to a member having the same function and configuration as those in FIG. 9, and the description will be omitted except for the following differences. As illustrated in this drawing, the magnetic sensor array 210 may be configured by arranging the plurality of magnetic sensor cells 220 in a U shape in a cross-sectional view when the plurality of magnetic sensor cells 220 are three-dimensionally arranged so as to be arranged at the lattice point between two curved surfaces, each of which is bent in one direction. More specifically, some of the magnetic sensor cells 220 may be arranged in a straight line outside the inscribed circle 910 and inside the circumscribed circle 920. Then, the remaining magnetic sensor cells 220 may be extended and arranged in the negative direction of the Z axis from each of the magnetic sensor cells 220 which are located at both ends of the straight line. Even in such a configuration, the centers of the inscribed circle and the circumscribed circle are common, and match with the coordinate origin in the signal separation calculation. The three-dimensional magnetic sensor array 210 having a curved surface shape used by the magnetic field measurement device 10 according to this embodiment includes those having such a shape.

Further, in the above description, a case where the magnetic field measurement device 10 reconstructs the magnetic field with respect to 64 places in total (8 places in the X axis direction×8 places in the Y axis direction) in the virtual sensor array plane has been described as an example. However, the invention is not limited to this. The magnetic field measurement device 10 may reconstruct the magnetic field in places more or less than 8 places in the X axis direction. Similarly, the magnetic field measurement device 10 may reconstruct a magnetic field in places more or less than 8 places in the Y axis direction. At this time, the number of places for reconstructing the magnetic field in the X axis direction may be different from the number of places for reconstructing the magnetic field in the Y axis direction. Further, the number of these places for reconstructing the magnetic field has no relationship with the number of actual sensor units 300 included in the magnetic sensor array 210. That is, the magnetic field measurement device 10 may reconstruct the magnetic field in places in a number more or less than the number of sensor units 300 actually included in the magnetic sensor array 210.

In addition, in the above description, a case where the magnetic field measurement device 10 reconstructs the magnetic field at equal intervals (2.5 cm) in the X axis direction and (2.5 cm) in the Y axis direction in the virtual sensor array plane has been described as an example. However, the invention is not limited to this. The magnetic field measurement device 10 may reconstruct the magnetic field at intervals more or less than 2.5 cm in the X axis direction. Similarly, the magnetic field measurement device 10 may reconstruct the magnetic field at intervals more or less than 2.5 cm in the Y axis direction. At this time, the interval in the X axis direction and the interval in the Y axis direction may be different. In addition, the magnetic field measurement device 10 may reconstruct the magnetic field at different intervals instead of equal intervals in at least one of the X axis direction and the Y axis direction.

In addition, in the above description, a case where the magnetic field measurement device 10 specifies the virtual sensor array plane in a plane parallel to the XY plane, and reconstructs the magnetic field of the Z axis component as a component orthogonal to the virtual sensor array plane has been described as an example. However, the invention is not limited to this. The magnetic field measurement device 10 may specify the virtual sensor array plane to a plane not parallel to the XY plane. In this case, the magnetic field measurement device 10 may synthesize the magnetic field vectors of the reconstructed three-axis components to acquire the magnetic field of a component orthogonal to the virtual sensor array plane.

In addition, in the above description, a case where the magnetic field measurement device 10 generates a current arrow map showing the current vectors at a plurality of positions on the virtual sensor array plane is illustrated as an example. However, the invention is not limited to this. The magnetic field measurement device 10 may generate, for example, an isointegral map, in which the current arrow map is integrated over time, as a current map. In addition, the magnetic field measurement device 10 may generate a map, from which a region surrounded by a closed curve where the integral value exceeds a predetermined threshold in the isointegral map (that is, a region where the electric activity of the heart is active) is extracted, as a current map. The magnetic field measurement device 10 according to this embodiment may generate such various derived maps as a current map.

Various embodiments of the invention may be described with reference to a flowchart and a block diagram. The block may be described as (1) a step of the process in which the operation is performed, or (2) a section of a device which serves to execute the operation. The specific step and section may be mounted in a dedicated circuit, a programmable circuit which is supplied together with a computer-readable instruction stored on a computer-readable medium, and/or a processor which is supplied together with a computer-readable instruction stored on the computer-readable medium. The dedicated circuit may include a digital and/or analog hardware circuit, or may include an integrated circuit (IC) and/or a discrete circuit. The programmable circuit may include a reconstructive hardware circuit including a logical AND, a logical OR, a logical XOR, a logical NAND, a logical NOR, memory elements such as other logical operations, flip-flops, registers, field programmable gate arrays (FPGAs), programmable logic arrays (PLAs), and the like.

The computer readable medium may include any tangible device that can store instructions executed by the appropriate device, and as a result, the computer-readable medium having instructions stored in the device includes an instruction that can be executed to create a means for performing the operation designated in a flowchart or block diagram, and becomes to include a product therein. Examples of the computer-readable medium may include electronic storage medium, magnetic storage medium, optical storage medium, electromagnetic storage medium, semiconductor storage medium, and the like. More specific examples of the computer-readable medium may include floppy (registered trademark) disks, diskettes, hard disks, random access memories (RAM), read-only memories (ROM), erasable programmable read-only memories (EPROM or flash memory), electrically erasable programmable read-only memories (EEPROM), static random access memories (SRAM), compact disk read-only memories (CD-ROM), digital versatile disks (DVD), Blu-ray (registered trademark) disks, memory sticks, integrated circuit cards, and the like.

The computer-readable instructions may include either source code or object code written in any combination of one or more programming languages, including assembler instructions, instruction set architecture (ISA) instructions, machine instructions, machine-dependent instructions, microcode, firmware instructions, state setting data, or object-oriented programming languages such as Smalltalk (registered trademark), JAVA (registered trademark), C++, etc., and traditional procedural programming languages such as "C" programming languages or similar programming languages.

The computer-readable instructions are provided locally or over a wide area network (WAN) such as a local area network (LAN), the Internet, etc., for processors or programmable circuits of general purpose computers, special purpose computers, or other programmable data processors. A computer-readable instruction may be executed to create a means for performing an operation specified in a flowchart or block diagram. Examples of processors include computer processors, processing units, microprocessors, digital signal processors, controllers, microcontrollers, and the like.

Figure 16:
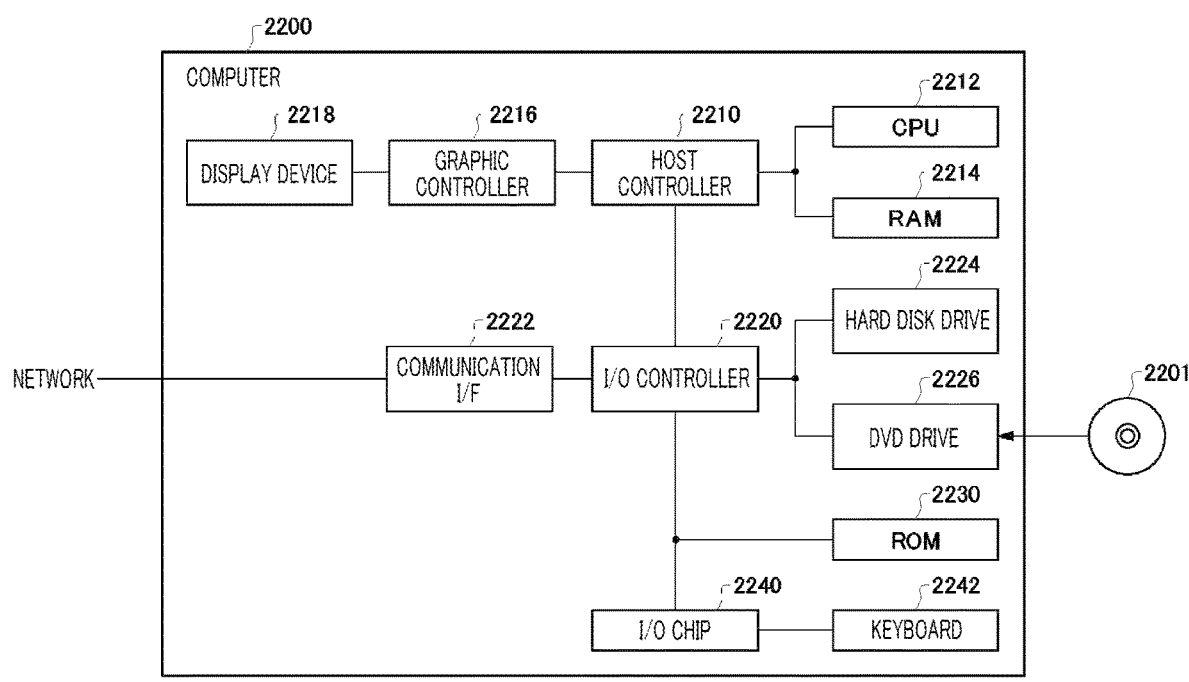
FIG. 16 illustrates an example of a computer 2200 in which a plurality of aspects of the invention may be embodied in whole or in part.

FIG. 16 illustrates an example of a computer 2200 in which a plurality of aspects of the present invention may be embodied in whole or in part. A program installed on the computer 2200 can cause the computer 2200 to perform operations associated with the device according to the embodiments of the invention or to function as one or more sections of the device, may cause the computer 2200 to perform the operations or the one or more sections, and/or can cause the computer 2200 to perform the process according to the embodiments of the invention or the steps of the process. Such a program may be executed by a CPU 2212 to have the computer 2200 perform a specific operation associated with some or all of the flowchart and the blocks of the block diagram described in this specification.

The computer 2200 according to this embodiment includes the CPU 2212, a RAM 2214, a graphic controller 2216, and a display device 2218, which are interconnected by a host controller 2210. The computer 2200 also includes input/output units such as a communication interface 2222, a hard disk drive 2224, a DVD-ROM drive 2226, and an IC card drive, which are connected to the host controller 2210 via an input/output controller 2220. The computer also includes a legacy input/output unit such as a ROM 2230 and a keyboard 2242, which are connected to the input/output controller 2220 via an input/output chip 2240.

The CPU 2212 operates according to a program stored in the ROM 2230 and RAM 2214, thereby controlling each unit. The graphic controller 2216 acquires image data generated by the CPU 2212 in a frame buffer or the like provided in the RAM 2214 or itself, so that the image data is displayed on the display device 2218.

The communication interface 2222 communicates with other electronic devices over a network. The hard disk drive 2224 stores programs and data used by the CPU 2212 in the computer 2200. The DVD-ROM drive 2226 reads the program or data from a DVD-ROM 2201 and provides the program or data to the hard disk drive 2224 via the RAM 2214. The IC card drive reads the program and data from the IC card and/or writes the program and data to the IC card.

The ROM 2230 stores in it a boot program or the like executed by the computer 2200 when activated, and/or a program that depends on the hardware of the computer 2200. The input/output chip 2240 may also connect various input/output units to the input/output controller 2220 via a parallel port, serial port, keyboard port, mouse port, or the like.

The program is provided by a computer-readable medium such as the DVD-ROM 2201 or IC card. The program is read from a computer-readable medium, installed on the hard disk drive 2224, the RAM 2214, or the ROM 2230, which are the examples of a computer readable medium, and executed by the CPU 2212. The information processing described in these programs is read on the computer 2200, resulting in cooperation between the program and the various types of hardware resources described above. The device or method may be configured by realizing the operation or processing of information according to the use of the computer 2200.

For example, when communication is performed between the computer 2200 and an external device, the CPU 2212 executes a communication program loaded into the RAM 2214 and may order the communication interface 2222 to perform communication processing based on the processing described in the communication program. Under the control of the CPU 2212, the communication interface 2222 reads the transmission data stored in the transmission buffer processing area provided within a recording medium such as the RAM 2214, hard disk drive 2224, DVD-ROM 2201, or IC card, transmits the read transmission data to the network, or writes reception data received from the network to a reception buffer processing area which is provided on the recording medium.

Further, the CPU 2212 may set all or necessary portions of files or database stored in an external recording medium such as the hard disk drive 2224, the DVD-ROM drive 2226 (DVD-ROM 2201), an IC card, or the like on the RAM 2214, and may perform various types of processing on the data on the RAM 2214. The CPU 2212 then writes back the processed data to the external recording medium.

Various types of information, such as various types of programs, data, tables, and databases, may be stored in the recording medium and processed. The CPU 2212 may perform various types of processing on data read from the RAM 2214 including various types of operations, information processing, conditional determination, conditional branching, unconditional branching, information search/replacement, etc., which are described throughout the present disclosure and designated by an instruction sequence of the program, and the results may be written back to the RAM 2214. Further, the CPU 2212 may search for information in a file, database, or the like in the recording medium. For example, in a case where a plurality of entries with attribute values for a first attribute respectively associated with an attribute value of a second attribute are stored in the recording medium, the CPU 2212 searches an entry that is matched with the condition among the plurality of entries, where the attribute value of the first attribute is specified, reads the attribute value of the second attribute stored in the entry, thereby the attribute value of the second attribute associated with the first attribute that satisfies the predetermined condition may be obtained.

The program or software module described above may be stored on the computer 2200 or in a computer-readable medium near the computer 2200. Further, a recording medium such as a hard disk or RAM provided in a dedicated communication network or a server system connected to the Internet can be used as a computer-readable medium, thereby providing a program to the computer 2200 via a network.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: magnetic field measurement device; 100: main body; 110: magnetic sensor unit; 120: head; 125: drive unit; 130: base portion; 140: pole portion; 142: support portion; 144: calibration magnetic field generation unit; 150: information processing unit; 210: magnetic sensor array; 220: magnetic sensor cell; 230: sensor data collection unit; 232: AD converter; 234: clock generator; 300: sensor unit; 520: magnetic sensor; 530: magnetic field generation unit; 532: amplification circuit; 534: feedback coil; 540: output unit; 710: magnetoresistive element; 720, 730: magnetic flux concentrator; 1000: sensor data processing unit; 1020: measurement data acquisition unit; 1030: synchronization detection unit; 1040: data output unit; 1050: basis vector storage unit; 1060: signal space separation unit; 1070: calibration clock generation unit; 1080: magnetic field reconstruction unit; 1090: current map generation unit; 2200: computer; 2201: DVD-ROM; 2210: host controller; 2212: CPU; 2214: RAM; 2216: graphic controller; 2218: display device; 2220: input/output controller; 2222: communication interface; 2224: hard disk drive; 2226: DVD-ROM drive; 2230: ROM; 2240: input/output chip; 2242: keyboard

What is claimed is:

1. A magnetic field measurement device, comprising:
at least one processor;
a magnetic sensor array that is composed of a plurality of magnetic sensor cells, each of which has a magnetic sensor and an output device for outputting an output signal, arranged at lattice points between two curved surfaces, each of which is bent in one direction, so as to be three-dimensionally arranged, and is capable of detecting an input magnetic field in three-axial directions;
a measurement data acquisition unit that uses the at least one processor to acquire measurement data measured by the magnetic sensor array; and
a magnetic field reconstruction unit that uses the at least one processor to reconstruct a magnetic field of a component orthogonal to a virtual sensor array plane with respect to one or more positions on the virtual sensor array plane, which is a plane specified in a three-dimensional space, using the measurement data.

2. The magnetic field measurement device according to claim 1, wherein:
each of the plurality of magnetic sensor cells further includes a magnetic field generation unit that uses the at least one processor generate a feedback magnetic field to reduce an input magnetic field detected by the magnetic sensor at a magnitude according to the output signal; and
the output device is configured to output the output signal according to a feedback current that flows for the magnetic field generation unit to generate the feedback magnetic field.

3. The magnetic field measurement device according to claim 2, wherein each of the magnetic sensors includes a magnetoresistive element and two magnetic flux concentrators that are arranged at both ends of the magnetoresistive element, and the magnetoresistive element is arranged at a position sandwiched by the two magnetic flux concentrators.

4. The magnetic field measurement device according to claim 3, wherein the magnetic field generation unit includes a feedback coil that is wrapped along an axial direction of a magnetic field to be detected by the magnetic sensor so as to surround the magnetoresistive element and the two magnetic flux concentrators.

5. The magnetic field measurement device according to claim 1, wherein:
the magnetic field reconstruction unit uses the at least one processor to reconstruct a magnetic field of a component orthogonal to the virtual sensor array plane with respect to a plurality of positions on the virtual sensor array plane; and
the magnetic field measurement device further comprises a current map generation unit using a magnetic field reconstructed with respect to the plurality of positions on the virtual sensor array plane that uses the at least one processor to generate a current map, in which a state of an active current due to an electrical activity of an object to be measured is projected onto the virtual sensor array plane.

6. The magnetic field measurement device according to claim 2, wherein:
the magnetic field reconstruction unit uses the at least one processor to reconstruct a magnetic field of a component orthogonal to the virtual sensor array plane with respect to a plurality of positions on the virtual sensor array plane; and
the magnetic field measurement device further comprises a current map generation unit using a magnetic field reconstructed with respect to the plurality of positions on the virtual sensor array plane that uses the at least one processor to generate a current map, in which a state of an active current due to an electrical activity of an object to be measured is projected onto the virtual sensor array plane.

7. The magnetic field measurement device according to claim 3, wherein:
the magnetic field reconstruction unit uses the at least one processor to reconstruct a magnetic field of a component orthogonal to the virtual sensor array plane with respect to a plurality of positions on the virtual sensor array plane; and
the magnetic field measurement device further comprises a current map generation unit using a magnetic field reconstructed with respect to the plurality of positions on the virtual sensor array plane that uses the at least one processor to generate a current map, in which a state of an active current due to an electrical activity of an object to be measured is projected onto the virtual sensor array plane.

8. The magnetic field measurement device according to claim 4, wherein:
the magnetic field reconstruction unit uses the at least one processor to reconstruct a magnetic field of a component orthogonal to the virtual sensor array plane with respect to a plurality of positions on the virtual sensor array plane; and
the magnetic field measurement device further comprises a current map generation unit using a magnetic field reconstructed with respect to the plurality of positions on the virtual sensor array plane that uses the at least one processor to generate a current map, in which a state of an active current due to an electrical activity of an object to be measured is projected onto the virtual sensor array plane.

9. The magnetic field measurement device according to claim 5, wherein the current map generation unit uses the at least one processor to generate a current arrow map showing current vectors at the plurality of positions based on a difference between a magnetic field reconstructed with respect to each of the plurality of positions on the virtual sensor array plane and a magnetic field reconstructed with respect to an adjacent position.

10. The magnetic field measurement device according to claim 1, further comprising a signal space separation unit that uses the at least one processor to perform a signal separation on a spatial distribution of the input magnetic field shown by the measurement data based on a basis vector which is calculated from an orthonormal function and a position and magnetic sensitivity of each magnetic sensor of the magnetic sensor array.

11. The magnetic field measurement device according to claim 2, further comprising a signal space separation unit that uses the at least one processor to perform a signal separation on a spatial distribution of the input magnetic field shown by the measurement data based on a basis vector which is calculated from an orthonormal function and a position and magnetic sensitivity of each magnetic sensor of the magnetic sensor array.

12. The magnetic field measurement device according to claim 3, further comprising a signal space separation unit that uses the at least one processor to perform a signal separation on a spatial distribution of the input magnetic field shown by the measurement data based on a basis vector which is calculated from an orthonormal function and a position and magnetic sensitivity of each magnetic sensor of the magnetic sensor array.

13. The magnetic field measurement device according to claim 4, further comprising a signal space separation unit that uses the at least one processor to perform a signal separation on a spatial distribution of the input magnetic field shown by the measurement data based on a basis vector which is calculated from an orthonormal function and a position and magnetic sensitivity of each magnetic sensor of the magnetic sensor array.

14. The magnetic field measurement device according to claim 5, further comprising a signal space separation unit that uses the at least one processor to perform a signal separation on a spatial distribution of the input magnetic field shown by the measurement data based on a basis vector which is calculated from an orthonormal function and a position and magnetic sensitivity of each magnetic sensor of the magnetic sensor array.

15. The magnetic field measurement device according to claim 9, further comprising a signal space separation unit that uses the at least one processor to perform a signal separation on a spatial distribution of the input magnetic field shown by the measurement data based on a basis vector which is calculated from an orthonormal function and a position and magnetic sensitivity of each magnetic sensor of the magnetic sensor array.

16. The magnetic field measurement device according to claim 10, wherein the magnetic field reconstruction unit uses the at least one processor to reconstruct a magnetic field of a measurement target magnetic field component, from which a disturbance magnetic field component is separated, with respect to one or more positions on the virtual sensor array plane, based on a result of the signal separation.

17. The magnetic field measurement device according to claim 1, wherein
a cardiac magnetic field, which is a magnetic field generated by an electrical activity of a heart, is a measurement target, and
a plane directly above a chest of an object to be measured is specified as the virtual sensor array plane.

18. The magnetic field measurement device according to claim 2, wherein
a cardiac magnetic field, which is a magnetic field generated by an electrical activity of a heart, is a measurement target, and
plane directly above a chest of an object to be measured is specified as the virtual sensor array plane.

19. A magnetic field measurement method, comprising:
acquiring measurement data that is measured by a magnetic sensor array that is composed of a plurality of magnetic sensor cells, each of which has a magnetic sensor and an output unit for outputting an output signal, arranged at lattice points between two curved surfaces, each of which is bent in one direction, so as to be three-dimensionally arranged, and is capable of detecting an input magnetic field in three-axial directions; and
reconstructing a magnetic field of a component orthogonal to a virtual sensor array plane with respect to one or more positions on the virtual sensor array plane, which is a plane specified in a three-dimensional space, using the measurement data.

20. A recording medium having a magnetic field measurement program recorded thereon, when executed by a computer, causing the computer to function as:
a measurement data acquisition unit that uses the at least one processor to that acquire measurement data measured by a magnetic sensor array that is composed of a plurality of magnetic sensor cells, each of which has a magnetic sensor and an output unit for outputting an output signal, arranged at lattice points between two curved surfaces, each of which is bent in one direction, so as to be three-dimensionally arranged, and is capable of detecting an input magnetic field in three-axial directions; and
a magnetic field reconstruction unit that uses the at least one processor to reconstruct a magnetic field of a component orthogonal to a virtual sensor array plane with respect to one or more positions on the virtual sensor array plane, which is a plane specified in a three-dimensional space, using the measurement data.

* * * * *